US 6,724,127 B2

(12) United States Patent
Takeuchi et al.

(10) Patent No.: US 6,724,127 B2
(45) Date of Patent: Apr. 20, 2004

(54) PIEZOELECTRIC/ELECTROSTRICTIVE DEVICE

(75) Inventors: Yukihisa Takeuchi, Nishikamo-Gun (JP); Takao Ohnishi, Nishikasugai-Gun (JP); Koji Kimura, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 10/231,737

(22) Filed: Aug. 30, 2002

(65) Prior Publication Data

US 2003/0011283 A1 Jan. 16, 2003

Related U.S. Application Data

(62) Division of application No. 09/214,110, filed as application No. PCT/JP98/03971 on Sep. 4, 1998, now Pat. No. 6,465,934.

(30) Foreign Application Priority Data

Sep. 8, 1997 (JP) .............................. 9-243073
Dec. 26, 1997 (JP) .............................. 9-361368

(51) Int. Cl.[7] .............................................. H01L 41/04
(52) U.S. Cl. ...................................................... 310/321
(58) Field of Search ................................ 310/328, 324, 310/332, 325

(56) References Cited

U.S. PATENT DOCUMENTS

| 3,739,202 | A | | 6/1973 | Cady |
| 4,383,763 | A | | 5/1983 | Hutchings et al. |
| 4,456,850 | A | * | 6/1984 | Inoue et al. ................. 310/324 |
| 4,613,782 | A | * | 9/1986 | Mori et al. ............. 310/323.16 |
| 4,685,767 | A | | 8/1987 | Ueshiba et al. |
| 5,323,228 | A | * | 6/1994 | Moody ........................ 356/469 |
| 5,523,643 | A | * | 6/1996 | Fujimura et al. ........... 310/328 |
| 5,773,916 | A | | 6/1998 | Nakamura et al. |
| 5,828,157 | A | * | 10/1998 | Miki et al. .................. 310/328 |

(List continued on next page.)

FOREIGN PATENT DOCUMENTS

| EP | 0 614 087 A2 | | 2/1994 | |
| JP | 61-46082 | | 3/1986 | |
| JP | 61-185982 | | 8/1986 | |
| JP | 62-201956 | | 12/1987 | |
| JP | 63-64640 | | 3/1988 | |
| JP | 63-224275 | * | 9/1988 | ........... H01L/41/08 |

(List continued on next page.)

OTHER PUBLICATIONS

S. Nakamura et al., *An Electrostatic Micro Actuator for a Magnetic Head Tracking System of Hard Disk Drives*, Transducers '97, 1997 International Conference on Solid–State Sensors and Actuators, Chicago, Jun. 16–19, 1997, pp. 1081–1084.

(List continued on next page.)

Primary Examiner—Burton S. Mullins
Assistant Examiner—Karen Beth Addison
(74) Attorney, Agent, or Firm—Burr & Brown

(57) ABSTRACT

A piezoelectric/electrostrictive device including a substrate and a connection plate having a first end joined to the substrate and an opposed second end extending along a first direction, and first and second opposed sides along a second direction perpendicular to the first direction. A fixing plate is joined to the second end of the connection plate. A first side of a first diaphragm is joined to the first side of the connection plate and an opposed second side of the first diaphragm is joined to the substrate. A first side of a second diaphragm is joined to the substrate and an opposed second side of the second diaphragm is joined to the second side of the connection plate. A piezoelectric/electrostrictive element is provided on at least a portion of at least one planar surface of at least one of the diaphragms.

23 Claims, 19 Drawing Sheets

U.S. PATENT DOCUMENTS

| | | | |
|---|---|---|---|
| 5,912,524 A | | 6/1999 | Ohnishi et al. |
| 5,942,837 A | * | 8/1999 | Reuter .................. 310/328 |
| 6,118,207 A | | 9/2000 | Ormerod et al. |
| 6,239,534 B1 | | 5/2001 | Takeuchi et al. |
| 6,307,299 B1 | | 10/2001 | Suzuki et al. |
| 6,326,563 B1 | * | 12/2001 | Takeuchi et al. ............ 310/321 |
| 6,386,053 B1 | | 5/2002 | Takeuchi et al. |
| 6,465,934 B1 | * | 10/2002 | Takeuchi et al. ............ 310/321 |
| 2002/0088284 A1 | | 7/2002 | Takeuchi et al. |

FOREIGN PATENT DOCUMENTS

| | | |
|---|---|---|
| JP | 64-351 | 1/1989 |
| JP | 64-35767 | 3/1989 |
| JP | 3-34259 | 4/1991 |
| JP | 4-62984 | 2/1992 |
| JP | 6-104503 | 4/1994 |
| JP | 6-164007 | 6/1994 |
| JP | 10-136665 | 5/1998 |

OTHER PUBLICATIONS

Kenji Uchino, *From Foundation up to Application of Piezoelectric/Electrostrictive Actuator*, Japan Industrial Technical Center, Morikita Shuppan, pp. 161–162.

* cited by examiner

FIG.7(a)
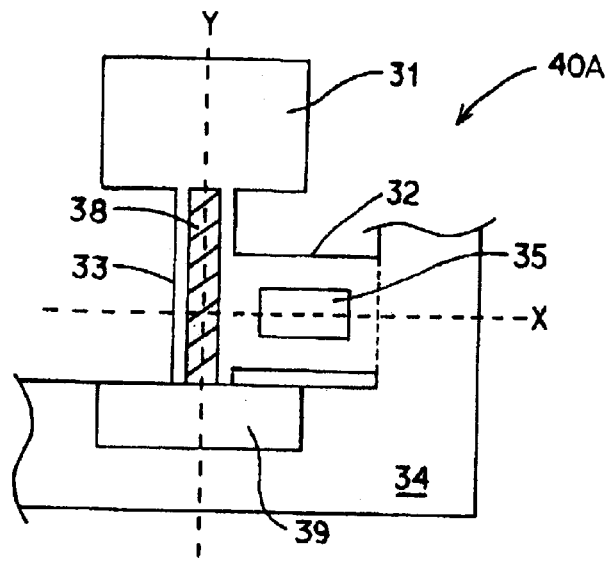
FIG.7(b)
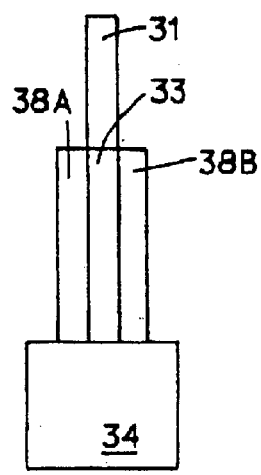
FIG.7(c)     FIG.7(d)     FIG.7(e)
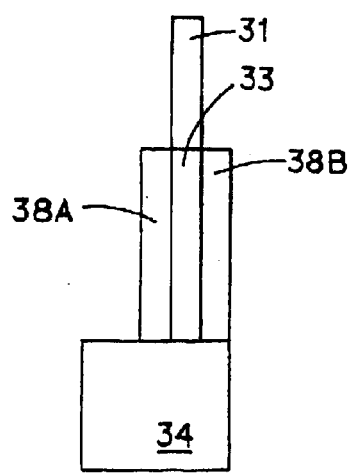 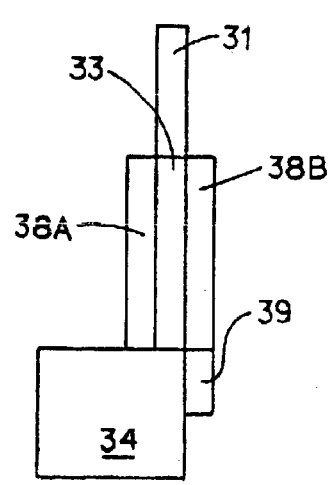 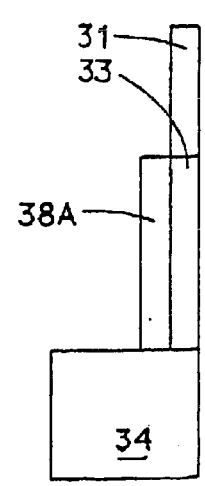

FIG.9(a)
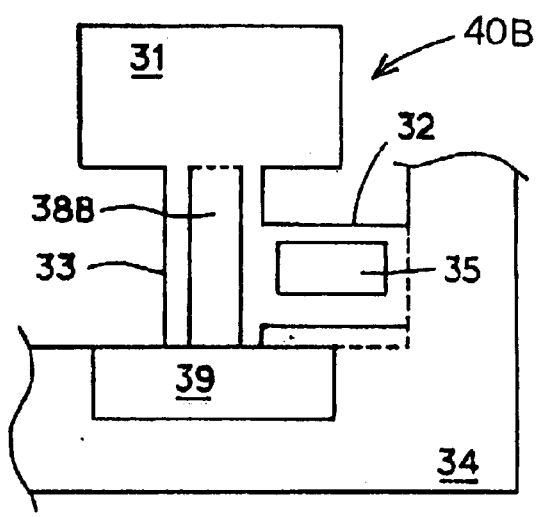
FIG.9(b)
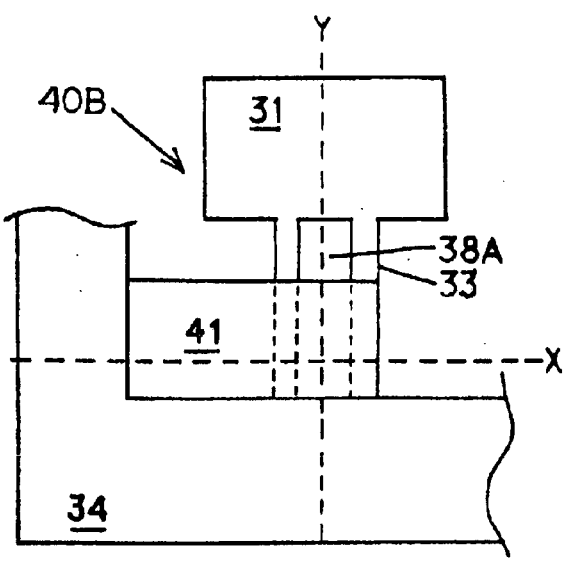
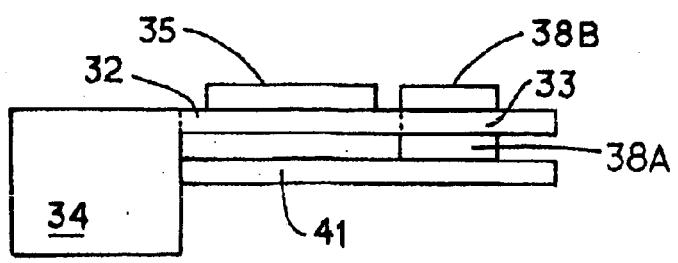
FIG.9(c)

FIG. 22
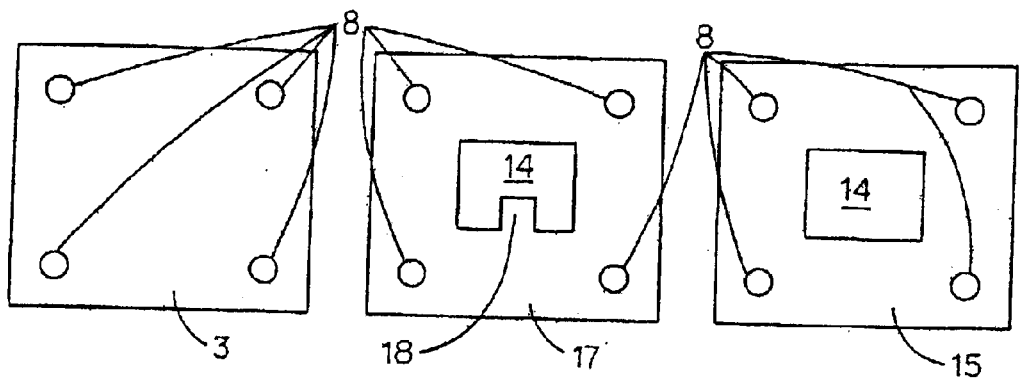
FIG. 23
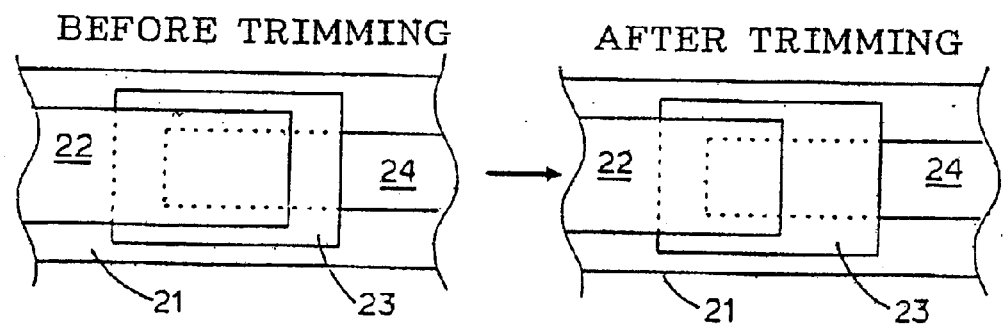
FIG. 24 - Prior Art
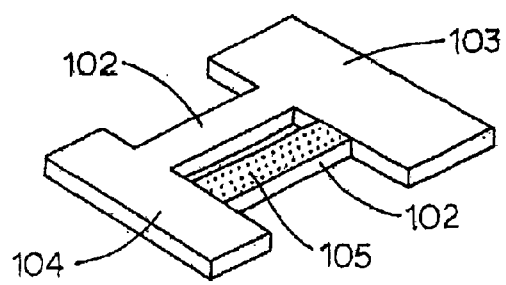

PIEZOELECTRIC/ELECTROSTRICTIVE DEVICE

CROSS REFERENCE TO RELATED APPLICATION

This application is a division of U.S. application Ser. No. 09/214,110, filed May 5, 1999, now U.S. Pat. No. 6,465,934, which was the National Stage of International Application No. PCT/JP98/03971, filed Sep. 4, 1998, the entireties of which are Incorporated herein by reference.

TECHNICAL FIELD

The present invention relates to a device using a piezoelectric/electrostrictive film, particularly to the structure of a piezoelectric/electrostrictive device for improving the operational characteristic of an element for converting electrical energy into mechanical energy such as mechanical displacement, mechanical force, or vibration and etc., and vice versa. Specifically, the present invention relates to a piezoelectric/electrostrictive device to be applied to transducers, various actuators, frequency-region functional components (filters), transformers, vibrators and resonators for communication and motive power, oscillators, discriminators, and various sensors including ultrasonic sensors, acceleration sensors, angular velocity sensors, impact sensors, and mass sensors, and moreover unimorph- and bimorph-type elements used for servo shift elements described in "From Foundation Up To Application of Piezoelectric/Electrostrictive Actuator" written by Kenji Uchino {edited by Japan Industrial Technical Center and published by MORIKITA SHUPPAN (transliterated)}, and to be preferably adopted to various actuators used for mechanisms for shift and positioning adjustment and angle adjustment of various precision components and etc. of optical equipment, precision equipment, etc.

BACKGROUND ART

Recently, a shift control element for adjusting an optical-path length or position on the sub-micron order has been requested in the optical and magnetic recording fields, as well as the precision-machining field. To respond to this request, piezoelectric/electrostrictive actuators have been developed, which are elements using a displacement based on the reverse or converse piezoelectric effect or electrostrictive effect caused by applying an electric field to a piezoelectric/electrostrictive material such as a ferroelectric.

In the field of magnetic recording on a hard disc drive, storage capacity has been remarkably increased in recent years. This is because an attempt has been made to use a recording medium more efficiently by increasing the number of recording tracks to increase the recording density. Recording methods have also improved.

This attempt has been mainly made so far in the area of the voice coil motor. Moreover, as a new technical art, an electrostatic-type microactuator micromachined in Si or Ni and used as the tracking system of a magnetic head for a hard-disk drive has been attempted, as described on pp. 1081–1084 in the preliminary manuscript collection of "1997 International Conference on solid-state Sensors and Actuators" of "TRANSDUCER'97".

Moreover, Japanese Patent Application Laid-Open No. 10-136665 discloses a piezoelectric actuator as shown in FIG. 24 in which a fixed portion 103, a movable portion 104, and at least one beam portion 102 for connecting the portions 103 and 104 to each other are integrally formed by forming at least one hole on a flat body made of a piezoelectric/electrostrictive material, and a strain generation portion is constituted by forming an electrode layer 105 on at least a part of at least one beam portion 102 so that an expansion or a contraction motion occurs in the direction connecting the fixed portion 103 with the movable portion 104, and a displacement mode of the movable portion 104 to the fixed portion 103 generated due to the expansion or contraction motion of the strain generation portion is an arc-shaped or rotational mode in the plane of the flat body.

However, in the case of the conventional art for positioning a recording head mainly using a voice coil motor, it is difficult to accurately position a recording head so as to accurately trace tracks when the number of tracks increases in order to correspond to a further increase in capacity.

The above-described technical art using an electrostatic-type microactuator obtains a displacement by applying a voltage between a plurality of flat electrodes formed through micromachining. However, it is difficult to increase a resonance frequency because of the structure. Consequently, the technical art includes such problems that vibrations are not easily attenuated when a high-speed operation is performed. Moreover, there is a feature that the technical art is displacement-theoretically inferior in the linearity of the voltage-displacement characteristic. Therefore, there are many problems to be solved from the viewpoint of accurate alignment. Furthermore, the process of micromachining itself has a problem from the viewpoint of the manufacturing cost.

Furthermore, in the case of a piezoelectric actuator disclosed in Japanese Patent Application Laid-Open No. 10-136665, the piezoelectric-operation portion has a monomorph structure. Therefore, the main-strain axis of a piezoelectric material becomes coaxial or parallel with the main-shift axis of the piezoelectric-operation portion. Thus, there are problems that the piezoelectric-operation portion itself generates only a small shift and the movable portion also shows a small displacement. Moreover, the piezoelectric actuator itself is heavy and subject to harmful vibrations for operation such as residual vibrations and vibrational noises under a high-speed operation as described in Japanese Patent Application Laid-Open No. 10-136665 and therefore, it is necessary to suppress harmful vibrations by injecting a filler into a hole. However, the use of such a filler may adversely influence displacement of the movable portion. Moreover, because it is unavoidable to constitute a piezoelectric actuator with a piezoelectric/electrostrictive material inferior in mechanical strength, there is a problem that the actuator is subject to material strength-imposed restrictions on shape and purpose.

SUMMARY OF THE INVENTION

The present invention is made to solve the problems of the above piezoelectric/electrostrictive device. According to the present invention, the following first to sixth piezoelectric/electrostrictive devices capable of accurately performing in-plane movements and operations at a high speed are provided.

That is, a piezoelectric/electrostrictive device in which a piezoelectric element is formed on at least a portion of at least one plane of a diaphragm whose one side is joined to a substrate and at least one side of one thin-walled fixing plate is joined to one side of the diaphragm so that the plane of the fixing plate and the plane of the diaphragm are perpendicularly intersected with each other, is provided as the first piezoelectric/electrostrictive device.

It is preferable that the first piezoelectric/electrostrictive device operates in accordance with at least either of a θ-mode displacement in which a fixing plate is displaced like a pendulum in the direction vertical to a side of the fixing plate and vertical to the vertical axis about the vertical axis vertically passing through the center of a fixed plane by using the joining face between the fixing plate and a diaphragm as the fixed plane and a φ-mode displacement in which a swing in the direction vertical to a side of the fixing plate and vertical to the vertical axis is displaced like a pendulum while being followed by a swing in the direction parallel with a side of the fixing plate, that is, the first piezoelectric/electrostrictive device drives the fixing plate by a piezoelectric element or detects the displacement amount of the fixing plate.

Moreover, a piezoelectric/electrostrictive device in which a fixing plate and a connection plate are joined with each other at their sides, and a diaphragm in which piezoelectric elements are arranged on at least a portion of at least one plane is joined to the connection plate at their sides in the direction perpendicular to the joining direction between the fixing plate and the connection plate, and at least parts of sides of the connection plate and the diaphragm are joined to a substrate, is provided as the second piezoelectric/electrostrictive device.

In this case, a part of a side of the connection plate to be joined to the substrate represents a side opposite to the connection face of the connection plate with the diaphragm. Therefore, the fixing plate and the substrate are connected with each other through the connection plate. A part of a side of the diaphragm to be joined to the substrate represents a side opposite to the connection face of the diaphragm to the connection plate or a side opposite to the connection face of the diaphragm to the fixing plate when the diaphragm is directly joined to the fixing plate. Moreover, the joining configuration between the connection plate or diaphragm and the substrate is common to piezoelectric/electrostrictive devices of the present invention to be described later.

Furthermore, a piezoelectric/electrostrictive device in which a fixing plate and a connection plate are joined with each other at their sides, and two diaphragms are joined at their sides so as to hold the connection plate in the direction perpendicular to the joining direction between the fixing plate and the connection plate, piezoelectric elements are arranged on at least a portion of at least one plane of at least one diaphragm, and at least parts of sides of the connection plate and each diaphragm are connected with a substrate is provided as the third piezoelectric/electrostrictive device.

In case of the third piezoelectric/electrostrictive device, it is preferable to arrange piezoelectric elements on at least one plane of one diaphragm and one or preferably, a plurality of slits on the other diaphragm. Moreover, in case of the second and third piezoelectric/electrostrictive devices, it is preferable to join other diaphragm plates in which piezoelectric elements are arranged at one end of a fixing plate at their sides and alternately join a necessary number of other connection plates and/or fixing plates and other diaphragms to the above other diaphragms at their sides to increase a displacement amount.

Then, a piezoelectric/electrostrictive device in which a connection plate and a diaphragm in which piezoelectric elements are arranged on at least a portion of at least one plane are not connected with each other but connected with a fixing plate at their sides in parallel and at least parts of the sides of the connection plate and the diaphragm are joined to a substrate is provided as the fourth piezoelectric/electrostrictive device.

Moreover, a piezoelectric/electrostrictive device in which a fixing plate joined to and held by two connection plates at sides is set between lateral sides of a concave portion formed on a substrate so as to be set between the lateral sides, two diaphragms are respectively set between each of the connection plates and the bottom sides of concave portion in the direction perpendicular to the direction for the connection plates to hold the fixing plate, and piezoelectric elements are arranged on at least a portion of at least one plane of at least one diaphragm is provided as the fifth piezoelectric/electrostrictive device. In this case, the concave portion represents a portion comprising facing sides and a bottom side for connecting these sides. In case of the present invention, it is not always necessary that a bottom side is a plane. It is possible to change the bottom side to various shapes by forming a recess or a protrusion on the bottom side as long as it does not influence the displacement of a fixing plate or measurement of a displacement amount.

Moreover, a piezoelectric/electrostrictive device in which a fixing plate is joined to and held by two connection plates at sides is set on a through-hole formed in a substrate, at least a plurality of diaphragms is bridged between each of the connection plate and the through-hole or between the fixing plate and the through-hole so as to span them in the direction perpendicular to the direction for the connection plates to hold the fixing plate, and piezoelectric elements are arranged on at least a portion of at least one plane of at least one of the diaphragm is provided as the sixth piezoelectric/electrostrictive device.

In case of the sixth piezoelectric/electrostrictive device, it is preferable to arrange piezoelectric elements on at least one plane of one diaphragm among pairs of diaphragms facing each other through each connection plate or a fixing plate and to form one or preferably, a plurality of slits on the other diaphragm.

In case of the second to sixth piezoelectric/electrostrictive devices, it is preferable to form a slit or constricted portion (narrow portion) on a connection plate because a displacement amount can be increased. Moreover, it is preferable to use a structure in which a diaphragm is fitted to and joined to a concave portion formed by a connection plate and a substrate. To obtain the above structure, it is preferable to integrally form a fixing plate, connection plate, and diaphragm from one diaphragm plate and form a substrate integrally with a diaphragm plate and a base plate by superimposing the diaphragm plate on the base plate. The concave portion represents a concave portion in which a substrate itself is formed into a concave shape, a concave portion in which a cutout is formed on a part of the outer periphery of a substrate, or a concave portion when regarding a part of a through-hole formed on a substrate as a concave portion.

Moreover, it is preferable to bond a spring plate with at least one plane of a connection plate and join the spring plate to a substrate or a spring-plate reinforcement portion. In this case, it is preferable that the spring plate is not bonded by using an adhesive or the like but the spring plate is formed integrally with an intermediate plate fitted between and integrated with a diaphragm plate and a base plate or formed integrally with a spring-plate reinforcement portion formed integrally with the diaphragm plate and also formed integrally with a connection plate. In case of the spring plate, when there are two or more connection plates, it is preferable that shapes formed by bonding connection plates with the spring plate become the same. Moreover, though the shape of the spring plate is not restricted, it is preferable to use a simple shape such as a pillar-shape or plate shape or a shape to be easily formed such as a U-shaped, H-shaped, or quadrangular frame because the manufacturing process can be simplified. Furthermore, it is preferable to use a reinforcement plate to be bonded with a spring plate and joined to a side of a substrate. In this case, it is preferable to form the reinforcement plate integrally with the spring plate and the substrate.

These second to sixth piezoelectric/electrostrictive devices respectively have a structure preferable to use either of a θ-mode displacement in which a fixing plate displaces like a pendulum in the direction vertical to a side of the fixing plate and vertical to the vertical axis vertically passing through the center of a fixed plane about the vertical axis by using the joining face between a connection plate and a substrate as the fixed plane and a φ-mode displacement in which a swing in the direction vertical to a side of the diaphragm and vertical to the vertical axis displaces like a pendulum while being followed by a swing in the direction parallel with a side of the fixing plate.

Moreover, in case of every piezoelectric/electrostrictive device described above, it is preferable to form a diaphragm and/or a connection plate by joining the diaphragm and/or connection plate to a side of an optional-shaped through-hole formed in a substrate because the piezoelectric/electrostrictive device can be easily handled and its damage can be avoided. Furthermore, it is preferable to divide one piezoelectric element into two parts and use one of them as a driving element and the other of them as an auxiliary element because it is possible to improve the positioning accuracy. In this case, the auxiliary element represents a trouble-shooting element, displacement confirming/deciding element, or auxiliary driving element. Furthermore, it is preferable to arrange piezoelectric elements on at least two places and use the piezoelectric element on at least one place as a driving element and the piezoelectric element on at least the other place as an auxiliary element because the driving accuracy and positioning accuracy are improved. Therefore, it is also possible to further divide each of piezoelectric elements arranged on two places or more into two parts.

Furthermore, it is preferable to cover each piezoelectric element, the electrode of the piezoelectric element, and an electrode lead to be connected to the electrode with an insulating coating layer made of resin or glass. Thus, even under a state in which a piezoelectric-element portion is soaked in a liquid, the electrode is not short-circuited and it is possible to use the piezoelectric/electrostrictive device. In this case, to improve the performance of the piezoelectric/electrostrictive device, it is preferable to use resin as an insulating coating material instead of glass, fluorocarbon resin superior in chemical stability is most preferably used, and it is also possible to preferably use silicon resin though this is inferior to fluorocarbon resin in chemical stability. When forming the above insulating coating layer, it is preferable to further form a shielding layer made of conductive materials on the surface of the insulating coating layer to minimize the influence of external noises such as electromagnetic waves.

It is preferable that substrate, fixing plate, connection plate, diaphragm, spring plate, spring-plate reinforcement portion, and reinforcement plate constituting a piezoelectric/electrostrictive device of the present invention are integrally formed by using a stabilized or partially-stabilized zirconia. A material mainly containing a component made of lead zirconate, lead titanate, and lead magnesium niobate is preferably used as the piezoelectric film of the piezoelectric element. Moreover, by trimming and adjusting the shape of a fixing plate, spring plate, or connection plate through laser-beam processing or cutting, it is possible to obtain a preferable shape each time depending on the type of an actuator to be applied. Furthermore, it is possible to easily adjust the displacement amount of a fixing plate. Furthermore, it is preferable to adjust the effective electrode area of the piezoelectric element by laser-beam-processing or cutting the electrode of a piezoelectric element, because a piezoelectric characteristic suitable for a use or a necessary spec can be easily obtained.

As the result of comparing a piezoelectric/electrostrictive device of the present invention with the piezoelectric actuator disclosed in Japanese Patent Application Laid-Open No. 10-136665, because the piezoelectric/electrostrictive device of the present invention has a unimorph- or bimorph-type structure having a diaphragm and thereby, the direction of the main-strain axis of a piezoelectric material is different from that of the main-displacement axis of a piezoelectric operating portion (portion causing a displacement by the strain of the piezoelectric material), it is found that the piezoelectric/electrostrictive device of the present invention has advantages that the strain of the piezoelectric material can be enlarged to the bending mode by effectively using the above feature and therefore, a large displacement of a fixing plate can be obtained. Moreover, a piezoelectric/electrostrictive device of the present invention allows functional differentiation and its substrate and the like other than its piezoelectric material can be constituted with a material mainly containing zirconia superior in mechanical strength and toughness. Therefore, there is an advantage that a compact, thin, and lightweight device having a desired strength can be obtained. Furthermore, a piezoelectric/electrostrictive device of the present invention has features that the displacing characteristic is not easily influenced from the outside and therefore, it is unnecessary to use a filler or the like.

The expression "piezoelectric" of piezoelectric element, piezoelectric film, and piezoelectric ceramics used for the present invention includes the meanings of both "piezoelectric" and "electrostrictive."

BRIEF DESCRIPTION OF DRAWINGS

FIGS. 5(a) to 5(c) show another embodiment of a piezoelectric/electrostrictive device of the present invention, in which FIG. 5(a) is a top view of the embodiment, FIG. 5(b) is an illustration of the θ mode, and FIG. 5(c) is an illustration of the φ mode;

FIGS. 7(a) to 7(e) show still another embodiment of a piezoelectric/electrostrictive device of the present invention, in which FIG. 7(a) is a top view of the embodiment and FIGS. 7(b) to 7(e) are sectional views of the embodiment;

FIGS. 9(a) to 9(c) show still another embodiment of a piezoelectric/electrostrictive device of the present invention, in which FIGS. 9(a) and 9(b) are top views of the embodiment and FIG. 9(c) is a sectional view of the embodiment;

FIGS. 16(a) and 16(b) show still another embodiment of a piezoelectric/electrostrictive device of the present invention, in which FIG. 16(a) is a top view of the embodiment and FIG. 16(b) is a sectional view of the embodiment;

FIGS. 18(a) to 18(d) show still another embodiment of a piezoelectric/electrostrictive device of the present invention, in which FIG. 18(a) is a top view of the embodiment and FIGS. 18(b) to 18(d) are sectional views of the embodiment;

FIGS. 21(a) to 21(f) show still another embodiment of a piezoelectric/electrostrictive device of the present invention, in which FIGS. 21(a) to 21(d) and FIG. 21(f) are top views of various structures respectively constituted by joining a diaphragm with a connection plate and FIG. 21(e) is a top view of a structure constituted by joining a diaphragm with a fixing plate;

FIG. 22 shows top views of worked green sheets for substrates used to fabricate a piezoelectric/electrostrictive device of the present invention;

FIG. 23 shows illustrations of a method for working a piezoelectric element of a piezoelectric/electrostrictive device of the present invention;

FIG. 24 shows a perspective view of a structure of a conventional piezoelectric/electrostrictive device (piezoelectric actuator)

BEST MODE FOR CARRYING OUT THE INVENTION

Figure 1A:
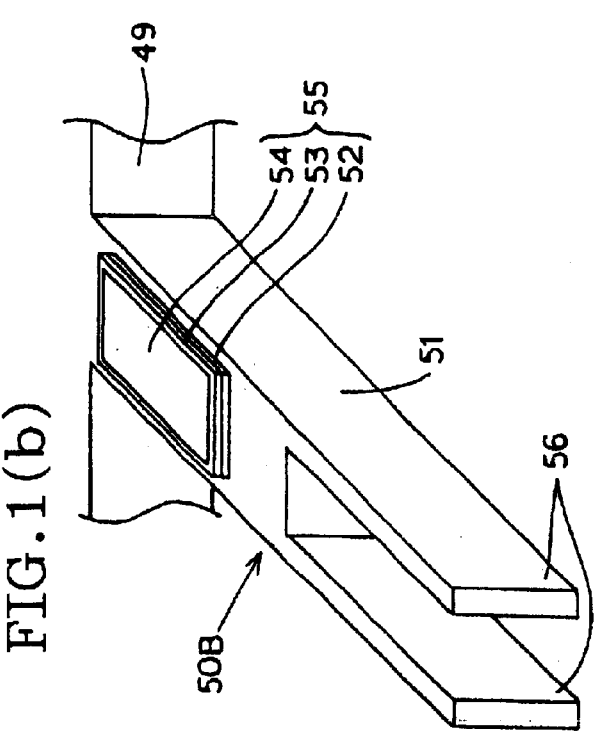
FIGS. 1(a) to 1(d) show perspective views of an embodiment of a piezoelectric/electrostrictive device of the present invention, in which the arrangement of and the number of fixing plates are changed.

FIG. 1(a) is a perspective view of an embodiment of a piezoelectric/electrostrictive device 50A of the present invention. The piezoelectric/electrostrictive device 50A has a shape in which a piezoelectric element 55 comprising a first electrode 52, a piezoelectric film 53, and a second electrode 54 is provided for one plane of a diaphragm 51 whose one side is joined to a substrate 49 and one side of a thin fixing plate 56 is joined to one side of the diaphragm 51 so that the plane of the fixing plate 56 and the plane of the diaphragm 51 are perpendicular to each other. In this case, it is also possible to provide the piezoelectric element 55 on both planes of the diaphragm 51 and thus, a lead portion (not illustrated) to be used for connection with a driving power supply or the like is connected to the first electrode 52 and the second electrode 54. Moreover, a side of the diaphragm 51 represents a plane vertical to the plane of the diaphragm 51 where the piezoelectric element 55 is set, that is, the thickness-directional plane and one side represents either of the sides.

By using the structure shown by the piezoelectric/electrostrictive device 50A, it is possible to displace the fixing plate 56 in the plane direction of the fixing plate 56 mainly. Specifically, the following are typical displacement modes: a displacement mode in which, when assuming the connection face between the fixing plate 56 and diaphragm 51 in FIG. 1(a) as a fixed plane, the fixing plate 56 displaces like a pendulum in the direction vertical to the side of the fixing plate 56 and vertical to Y-axis, that is, in X-axis direction centering around the vertical axis (Y-axis) vertically passing through the center of the fixed plane (this displacement mode is hereafter referred to as "θ mode"), a displacement mode in which the fixing plate 56 displaces like a pendulum in X-axis direction centering around Y-axis so that the component of swing in Z-axis direction parallel with the side of the fixing plate 56 increases as away from Y-axis (this displacement mode is hereafter referred to as "φ mode"), and a telescopic displacement mode in Y-axis direction.

These displacement modes represent that the displacement direction of the fixing plate 56 is dominant in the above-described directions but a directional component other than described directions is not completely excluded. The same is true for a case of referring to displacement modes of various embodiments described below.

When considering application of a magnetic head, it is preferable that the head does not exhibit three-dimensional displacement so as to keep the space (gap) between the head and a recording medium. The piezoelectric/electrostrictive device 50A displacing in the θ mode or telescopic displacement mode is a device suitable for the above purpose. When using the piezoelectric/electrostrictive device 50A for an acceleration sensor other than a magnetic head, it is a matter of course to use the φ mode in addition to the above modes. The relation between the dimension of each displacement mode and a purpose is common to the configuration of every piezoelectric/electrostrictive device of the present invention.

Figure 1B:
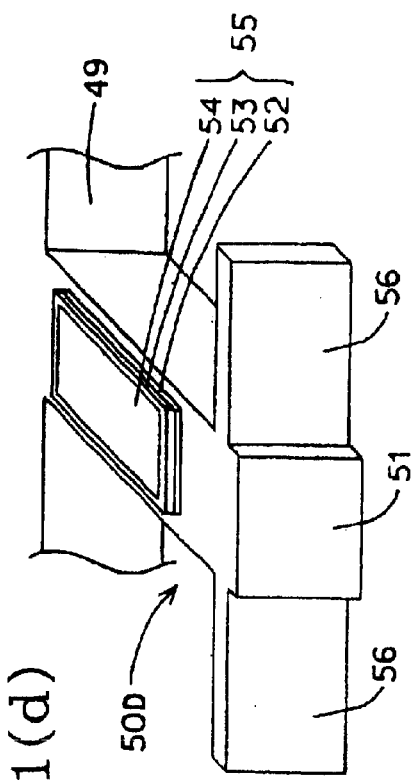
Figure 1C:
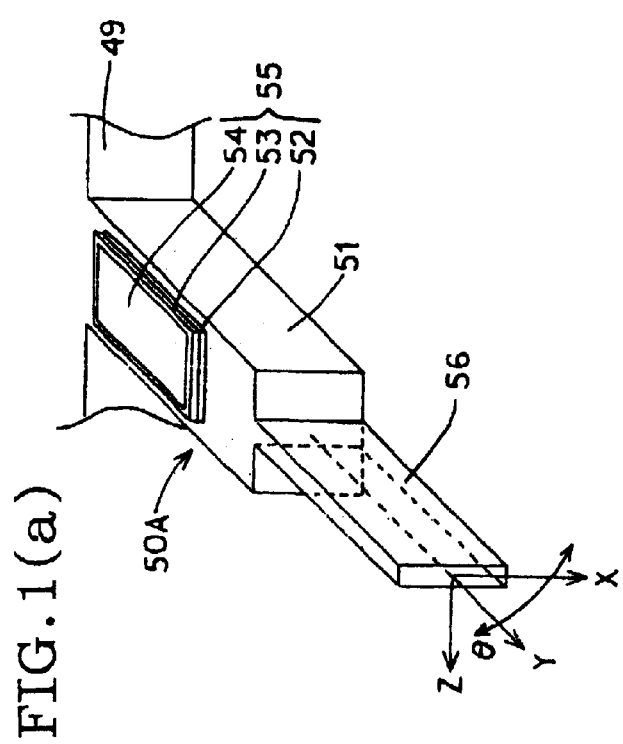
Figure 1D:
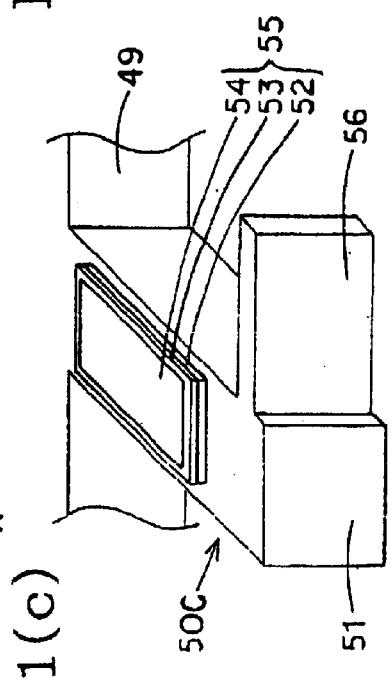

FIGS. 1(b) to 1(d) show other embodiments using the operation principle of the piezoelectric/electrostrictive device 50A. Here, the piezoelectric/electrostrictive device 50B shown in FIG. 1(b) is configured by setting two fixing plates 56 in FIG. 1(a) to one side of the diaphragm 51 in parallel. Therefore, it is possible to use a plurality of fixing plates 56 and thus, it is possible to use a necessary number of fixing plates according to the purpose.

Joining positions between a plurality of fixing plates 56 and the diaphragm 51 can be set to any side other than the joining side between the substrate 49 and the diaphragm 51. Moreover, it is enough that at least one fixing plate 56 is set.

Therefore, in case of the piezoelectric/electrostrictive device 50C shown in FIG. 1(c), it is also possible to join the fixing plate 56 to the side vertical to the joining side between the diaphragm 51 and the substrate 49 among the sides of the diaphragm 51. Moreover, in case of the piezoelectric/electrostrictive device 50D shown in FIG. 1(d), it is possible to set two fixing plates 56 on opposite sides of diaphragm 51.

Figure 2:
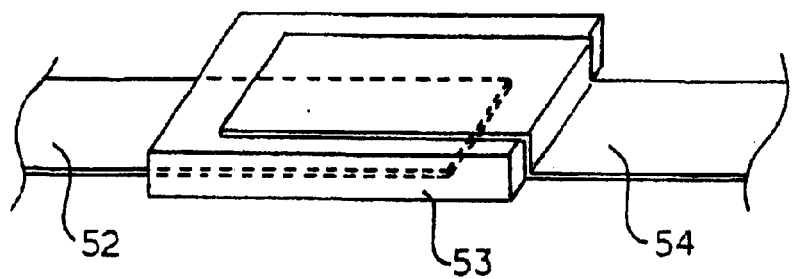
FIG. 2 shows a perspective view of an embodiment of a piezoelectric element to be used for a piezoelectric/electrostrictive device of the present invention.
Figure 3:
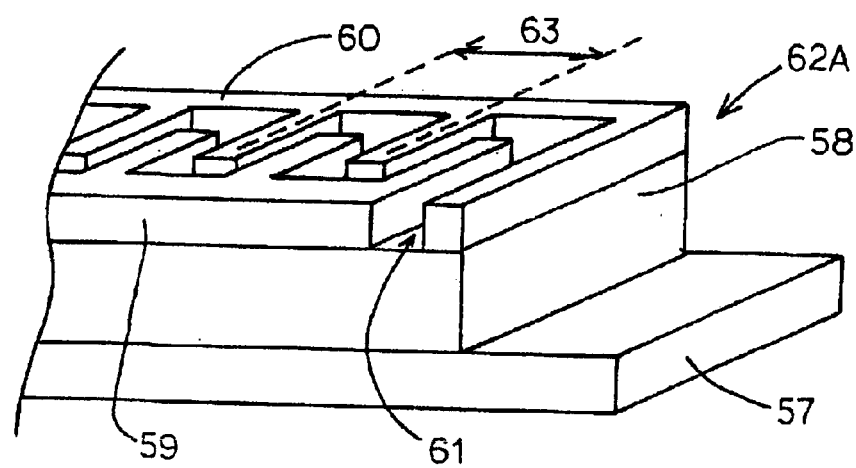
FIG. 3 shows a perspective view of another embodiment of a piezoelectric element to be used for a piezoelectric/electrostrictive device of the present invention.

The laminar-type configuration obtained by forming the first electrode 52, piezoelectric film 53, and second electrode 54 into a layer shown in FIG. 2 is typical as the configuration of the piezoelectric element 55 used for the piezoelectric/electrostrictive devices 50A to 50D described above. Moreover, as shown in FIG. 3, it is possible to use a piezoelectric element 62A having comb-shaped electrodes in which a piezoelectric film 58 is formed on a diaphragm 57 and a first electrode 59 and a second electrode 60 form a gap portion 61 having a certain width on the piezoelectric film 58. The first electrode 59 and second electrode 60 in FIG. 3 can be also formed between the diaphragm 57 and the piezoelectric film 58. Moreover, as shown in FIG. 4, a piezoelectric element 62B is preferably used which is configured by embedding the piezoelectric film 58 between the comb-shaped first electrode 59 and second electrode 60.

Figure 4:
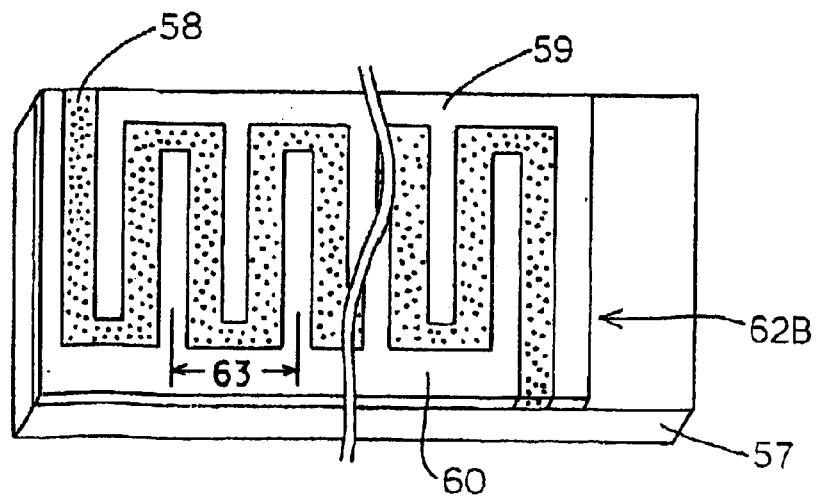
FIG. 4 shows a perspective view of still another embodiment of a piezoelectric element to be used for a piezoelectric/electrostrictive device of the present invention.

In this case, when using the comb-shaped electrodes shown in FIGS. 3 and 4, it is possible to increase a displacement by decreasing a pitch 63. The piezoelectric elements shown in FIGS. 2 to 4 can be applied to every piezoelectric/electrostrictive device of the present invention to be mentioned later.

The piezoelectric/electrostrictive devices 50A to 50D described above are disadvantageous for decrease in size and weight and moreover, easily cause a trouble that a warpage or curve occurs on the fixing plate 56 and it is difficult to adjust a displacement mode. Therefore, it is preferable to use the devices 50A to 50D by changing their structures to the structure shown in FIG. 5(a) because these problems are solved.

Figure 5A:
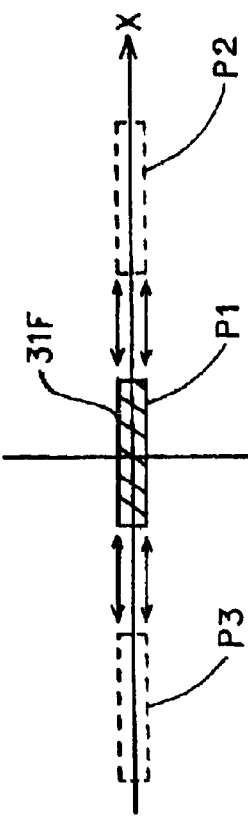

FIG. 5(a) is a top view of another embodiment of a piezoelectric/electrostrictive device of the present invention. The piezoelectric/electrostrictive device 30 has a structure in which a fixing plate 31 and a connection plate 33 are joined with each other at their sides, a diaphragm 32 is joined to the connection plate 33 at their sides in the direction perpendicular to the Y-axis direction serving as the direction of joining between the fixing plate 31 and the connection plate 33, that is, the X-axis direction, a piezoelectric element 35 is set on one plane of the diaphragm 32, and parts of sides of the connection plate 33 and diaphragm 32 are joined to a side of the substrate 34. In this case, it is also possible to form the piezoelectric element 35 on the both planes of the diaphragm 32 and use one of the above-described various piezoelectric elements shown in FIGS. 2 to 4 as the piezoelectric element 35.

It is not always necessary for the fixing plate 31, connection plate 33, and diaphragm 32 to have the same thickness. This is because any one of various shapes can be selected as the shape of the fixing plate 31 as described later. However, it is preferable to integrally form the fixing plate 31, connection plate 33, and diaphragm 32 and moreover, it is preferable to form a side of the connection plate 33 and the diaphragm 32 integrally with the substrate 34. This integral structure can be easily obtained through the lamination method using ceramic green sheets to be mentioned later.

It is possible to operate the piezoelectric/electrostrictive device 30 in at least any one of the bending mode in which the fixing plate 31 displaces so as to bend in the Z-axis direction (not illustrated) vertical to the X-axis and the Y-axis, the axis rotation mode in which the fixing plate 31 displaces so as to rotate by using the Y-axis as a base axis, the θ mode in which the fixing plate 31 displaces like a pendulum in the X-axis direction so that the fixing plate 31 forms a certain angle θ from the Y-axis centering around the Y-axis in the plane of the plate 31, and the φ mode in which the fixing plate 31 displaces like a pendulum in the X-axis direction centering around the Y-axis so that the component of swing in the Z-axis direction (not illustrated) parallel with a side of the fixing plate 31 increases as away from the Y-axis.

Figure 5B:
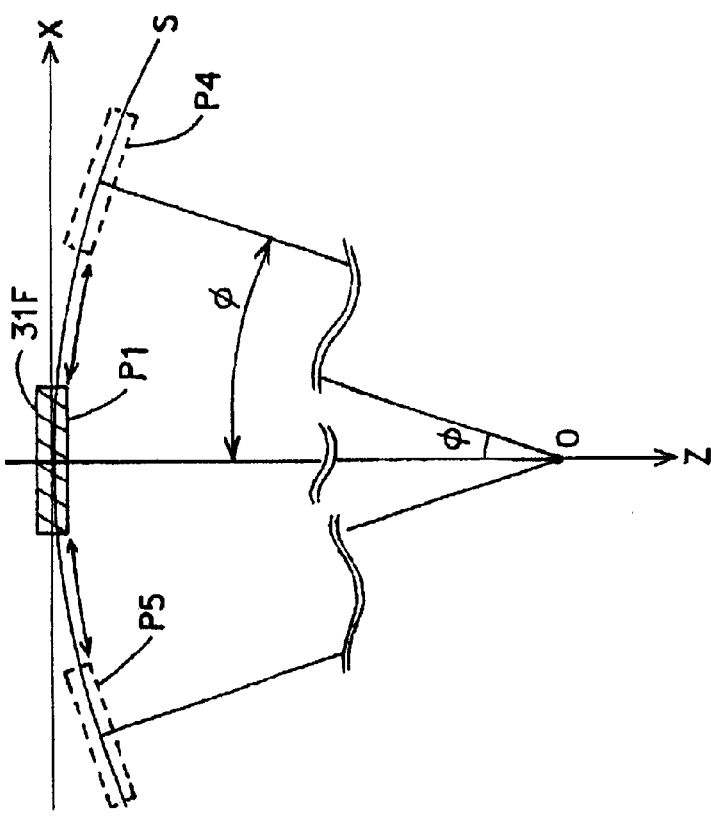

The above θ mode and φ mode are described below in more detail. FIG. 5(b) is a top view for explaining the θ mode, which shows movement of the fixing plate 31 when viewing the piezoelectric/electrostrictive device 30 in FIG. 5(a) from the direction of arrows AA in FIG. 5(a), that is, from the Y-axis direction on the X-axis. In this case, the upper end face 31F of the fixing plate 31 is present at a position P1 when it does not displace. As described above, however, in the θ mode, the fixing plate 31 displaces like a pendulum in the X-axis direction centering around the Y-axis in the plane of the fixing plate 31, that is, the X-Y plane so as to form a certain angle θ from the Y-axis. In this case, from the direction of arrows AA, it is possible to show the movement of the upper end face 31F of the fixing plate 31 as a displacement reciprocating between positions P2 and P3 on the X-axis and the displacement motion is defined as θ mode.

Figure 5C:
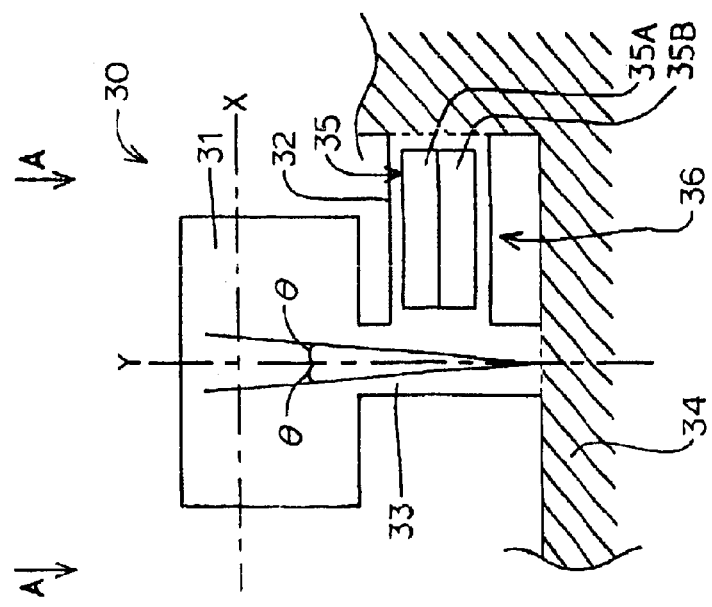

FIG. 5(c) is a top view for explaining the φ mode and shows the movement of the fixing plate 31 when viewing the piezoelectric/electrostrictive device 30 in FIG. 5(a) from the direction of arrows AA in FIG. 5(a) similarly to the case of FIG. 5(b). Also in FIG. 5(c), the upper end face 31F of the fixing plate 31 is present at the position P1 when it does not vibrate. As described above, in the φ mode, the fixing plate 31 displaces like a pendulum centering around the Y-axis in the X-axis direction and displaces so that the component of swing in the Z-axis direction parallel with a side of the fixing plate 31 increases as away from the Y-axis. That is, the movement of the upper end face 31F of the fixing plate 31 from the direction of arrows AA is shown as a displacement reciprocating between a position P4 and a position P5 on a circular-arc orbit S passing through the position P1 when assuming a point on the Z-axis as center O. In this case, an angle formed between the straight line connecting the fixing plate 31 and the center O and the Z-axis is φ and the above displacement motion is defined as φ mode.

In the case of the piezoelectric/electrostrictive device 30, it is also possible to divide one piezoelectric element 35 so that two piezoelectric elements 35A and 35B are formed in the Y-axis direction. Moreover, it is possible to set two piezoelectric elements on the both planes of the diaphragm 32 one each. In this case, it is preferable to use one piezoelectric element 35A as a driving element to make the fixing plate 31 cause a predetermined displacement and the other piezoelectric element 35B as an auxiliary element, for example, for confirming whether a predetermined displacement amount is obtained, that is, an auxiliary element is preferably used as a displacement confirmation/decision element, trouble-shooting element, or auxiliary driving element for detecting the displacement of the driving piezoelectric element 35A and applying feedback to driving signals for the driving piezoelectric element 35A so that a predetermined displacement can be obtained when a voltage applied to the driving piezoelectric element 35A does not reach a predetermined voltage amount due to any cause, because the driving accuracy, positional accuracy, and detection accuracy can be improved.

To divide one piezoelectric element 35, it is possible to use any one of a method for setting the element 35 and thereafter dividing the element 35 through laser-beam processing and a method for dividing the piezoelectric element 35 and thereafter setting it. The arrangement of a plurality of piezoelectric elements and the division and usage of each piezoelectric element 35 can be applied to every piezoelectric/electrostrictive device of the present invention.

Figure 6A:
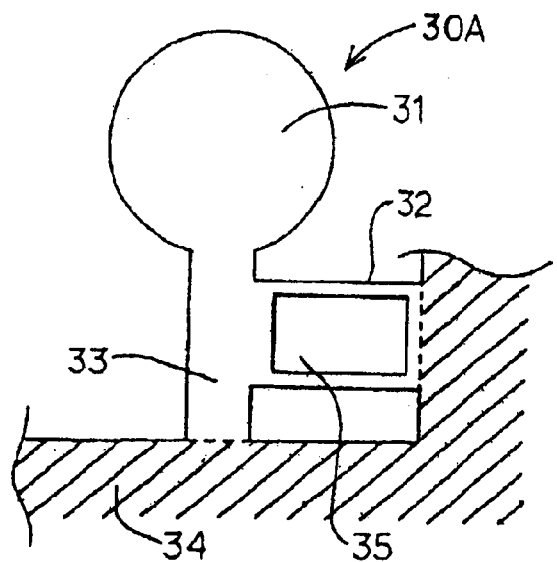
FIGS. 6(a)–(d) show top views showing still another embodiment of a piezoelectric/electrostrictive device of the present invention.
Figure 6B:
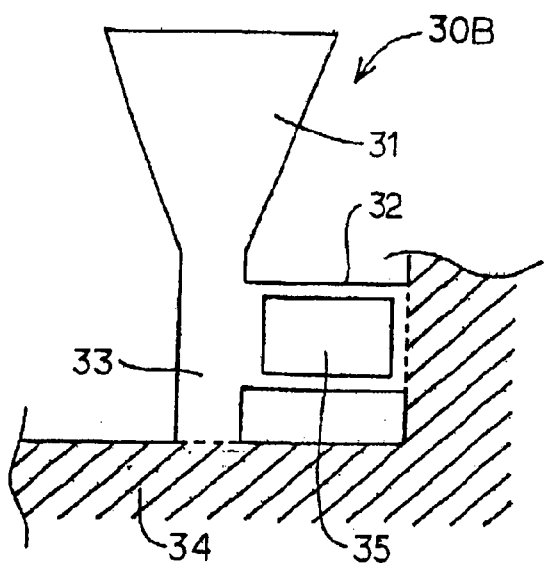
Figure 6C:
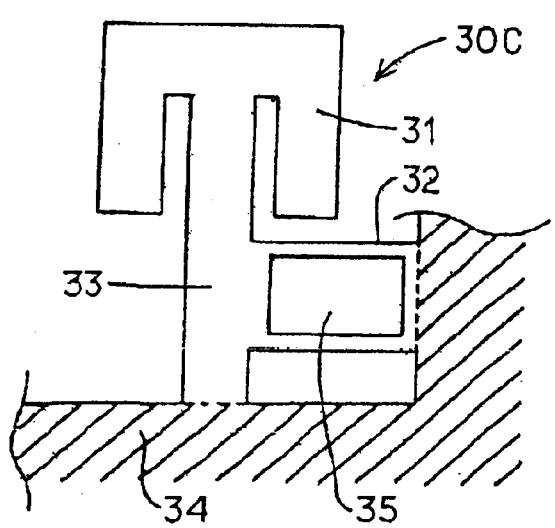
Figure 6D:
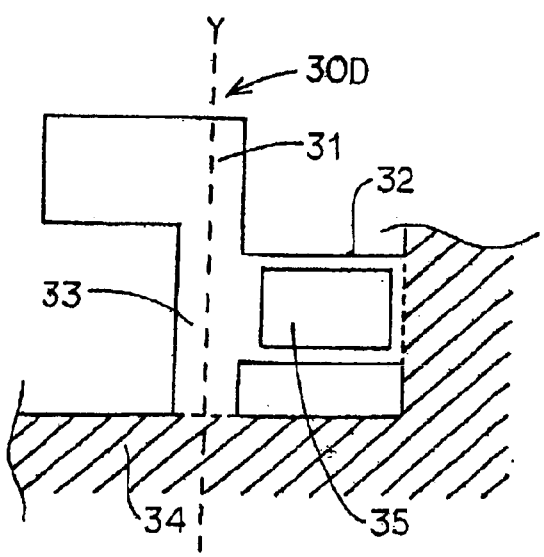

The shape of the plane of the fixing plate 31 of the above piezoelectric/electrostrictive device 30 is not restricted to the rectangle shown in FIG. 5(a). As shown by the piezoelectric/electrostrictive devices 30A to 30C in FIGS. 6(a) to 6(c), it is possible to use various optional shapes such as circle, triangle, inverse-concave shape, polygon, ellipse, and long circle. Moreover, it is unnecessary to join the fixing plate 31 so as to be symmetric to the connection plate 33 with respect to the Y-axis as shown by the piezoelectric/electrostrictive device 30D in FIG. 6(d). That is, it is possible to optionally select the shape of the fixing plate 31 in accordance with various sensors, a recording head, or other structures used in combination with the piezoelectric/electrostrictive device.

Then, in the case of the present invention, it is possible to preferably use a structure in which a spring plate is bonded with one plane or both planes of a connection plate and the spring plate is joined to a sensor substrate or a spring-plate reinforcement portion. FIG. 7(a) is a top view of a piezoelectric/electrostrictive device 40A which is an embodiment constituted by setting a prismatic spring plate 38 and a spring-plate reinforcement portion 39 to the above piezoelectric/electrostrictive device 30. Moreover, FIGS. 7(b) to 7(e) are sectional views showing the arrangement of the spring plate 38 and the spring-plate reinforcement portion 39 viewed from the X-axis direction on the Y-axis.

The spring plate 38 is joined to at least one plane of the connection plate 33 and its width can be narrower than or equal to that of the connection plate 33 as shown in FIG. 7(a). Moreover, to set the spring plates 38 made of the same material to the both plane of the connection plate 33 one each, it is preferable to equalize the shapes of the spring plates 38. However, to apply spring plates 38 made of materials different from each other to planes of the connection plate 33 one each, it is unnecessary to equalize the shapes of the spring plates 38 each other. It is possible to form each spring plate 38 into a proper shape by considering the Young's modulus of each spring plate 38.

The spring plate 38 is also joined to the substrate 34 in principle. In this case, it is decided whether it is necessary or not to set the spring-plate reinforcement portion 39 depending on the joining position of the connection plate 33 with the substrate 34. That is, as shown in FIGS. 7(b) and 7(c), when the connection plate 33 is joined to a position where the spring plate 38 can be directly joined to the substrate 34, it is unnecessary to separately set the spring-plate reinforcement portion 39 because the substrate 34 also functions as the spring-plate reinforcement portion 39. Moreover, in this case, it is possible to set the spring plate 38 only to one plane of the connection plate 33.

However, as shown in FIG. 7(d), when the connection plate 33 is joined to an end of the substrate 34, it is preferable to set the spring-plate reinforcement portion 39 to the spring plate 38B as a portion for supporting the spring plate 38B though the substrate 34 also functions as the spring-plate reinforcement portion 39 in the case of the spring plate 38A. Moreover, as shown in FIG. 7(e), even when the connection plate 33 is joined to an end of the substrate 12, it is not necessary to form the spring-plate reinforcement portion 39 when only the spring plate 38A is joined to the substrate 12 and the spring plate 38B is not used.

By setting the spring plate 38, the mechanical strength of the connection plate 33 is improved. Moreover, in case of setting the spring plate 38 to the both planes of the connection plate 33, it is possible to displacement the center of gravity of a portion constituted of the connection plate 33 and the spring plate 38 when displacing the fixing plate 31 by the piezoelectric/electrostrictive device 35. Therefore, the fixing plate 31 is easily displaced to the θ mode and this is preferable for the purpose such as a magnetic head or the like. Moreover, an advantage of improving the rigidity and the high-speed response characteristic of a piezoelectric/electrostrictive device can be obtained.

Figure 8A:
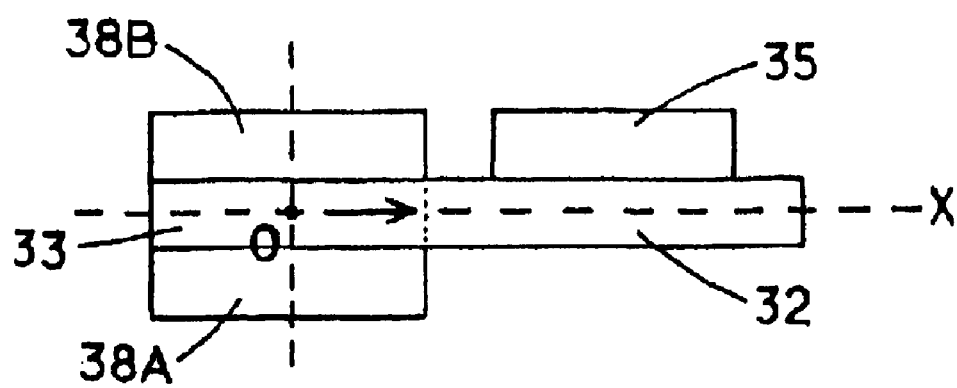
FIGS. 8(a)–(b) show illustrations related to driving of a piezoelectric/electrostrictive device of the present invention.
Figure 8B:
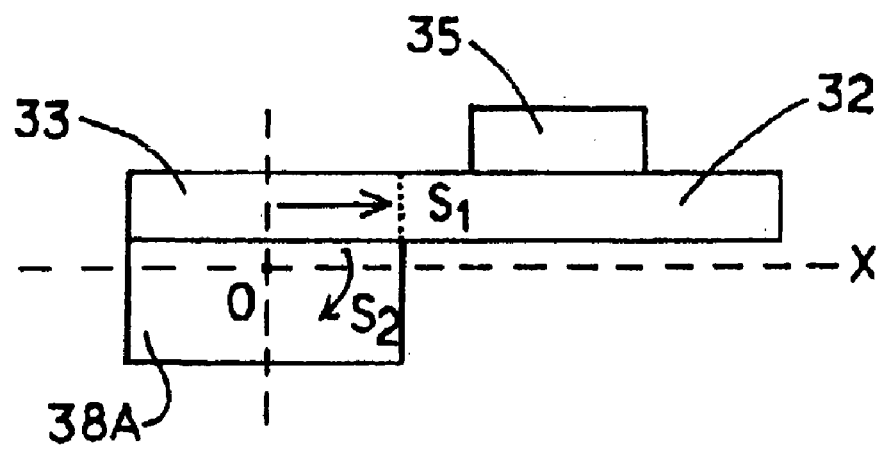

That is, as sectional views viewed from the Y-axis direction on the X-axis in FIGS. 7(c) and 7(d) are shown in FIGS. 8(a) and 8(b), the fixing plate 31 easily displaces in the X-axis direction, that is in the θ mode in FIG. 8(a) because the piezoelectric/element 35 is able to displace the center O of the spring plates 38A and 38B and the connection plate 33 in the X-axis direction. However, in FIG. 8(b), since the center O of the spring plates 38A and 38B and the connection plate 33 is not present on the connection plate 33, the driving force of the piezoelectric element 35 in the X-axis direction (arrow $S_1$) is added to the center O as a torque (arrow $S_2$) and the displacement of the axis rotation mode easily occurs though the rotation mode is restricted due to the rigidity of the spring plate 38A.

Thus, when setting the spring plate 38, it is preferable to further set a reinforcement plate 41 to be bonded with the spring plate 38 and joined to a side of the substrate 34 like the case of the piezoelectric/electrostrictive device 40B shown in FIG. 9. Here, FIGS. 9(a) and 9(b) show top views of the piezoelectric/electrostrictive device 40B viewed from the surface and the back of it and FIG. 9(c) shows a sectional view of the device 40B viewed from the Y-axis direction on the X-axis in FIG. 9(b). In this case, the reinforcement plate 41 is bonded to the spring plate 38A bonded to the connection plate 33 and joined to the squarely-cut-out side of the substrate 34. Moreover, it is preferable that the reinforcement plate 41 is formed integrally with the spring plate 38 and the substrate 34.

It is needless to say that the above spring plate can be applied to every piezoelectric/electrostrictive device of the present invention in which a connection plate is used as a component member. Moreover, as described later in a method for fabricating a piezoelectric/electrostrictive device of the present invention, it is preferable that the spring plate is formed integrally with an intermediate plate inserted between and integrated with a diaphragm plate and a base plate or formed integrally with a spring-plate reinforcement portion formed integrally with the diaphragm plate and also formed integrally with each connection plate.

Figure 10A:
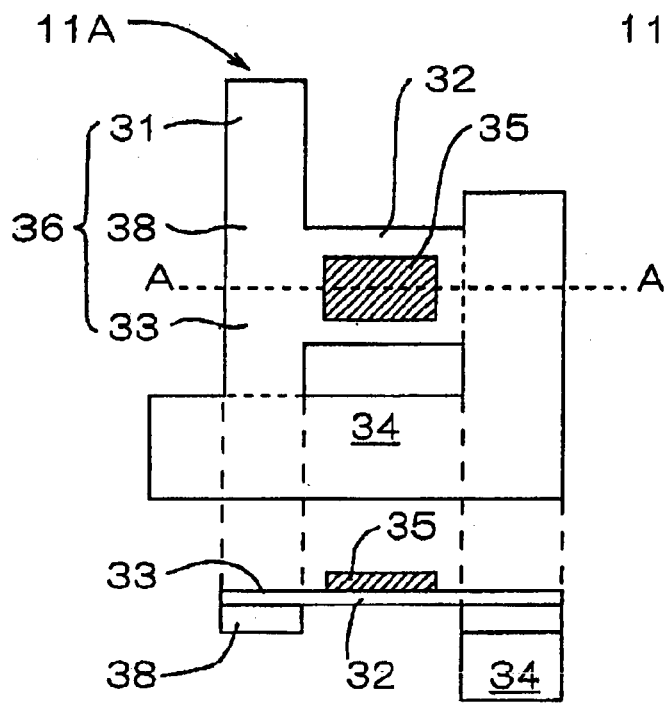
FIGS. 10(a)–(d) show top views of still another embodiment of a piezoelectric/electrostrictive device of the present invention.

FIGS. 10(a) to 10(d) show still another embodiment of a piezoelectric/electrostrictive device of the present invention. FIG. 10(a) shows a sectional view of a piezoelectric/electrostrictive device 11A and a sectional view taken along the broken line A—A of the top view. In the case of the piezoelectric/electrostrictive device 11A, a spring plate 38 is bonded to a connection plate 33 and a fixing plate 31 has a shape formed by extending the connection plate 33 and the spring plate 38 in the Y-axis direction. Therefore, the boundary between the fixing plate 31 and the connection plate 33 or the spring plate 38 is not clear. A structure obtained by integrating the fixing plate 31, connection plate 33, and spring plate 38 is the same as the case of the piezoelectric/electrostrictive devices 11B to 11D shown in FIGS. 10(b) to 10(d) and hereafter referred to as a connection-fixing plate 36. By forming the connection-fixing plate 36 into a thick and slender shape, it is possible to prevent displacement modes such as bending mode and axis rotation mode from occurring.

Figure 10B:
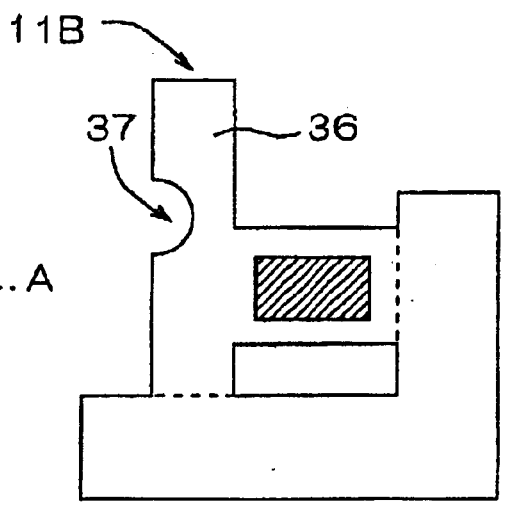
Figure 10C:
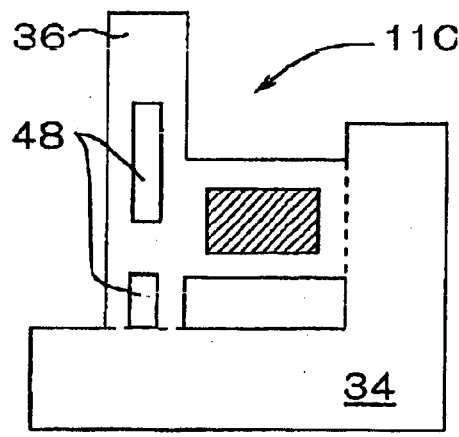
Figure 10D:
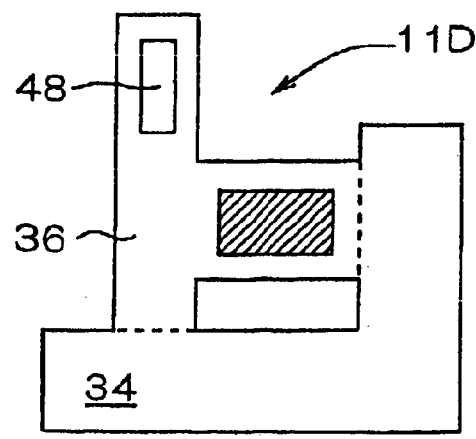

In the case of the piezoelectric/electrostrictive device 11B shown in FIG. 10(b), a constricted portion 37 is provided for the connection-fixing plate 36. Moreover, in the case of the piezoelectric/electrostrictive device 11C shown in FIG. 10(c), a slit 48 is formed for the connection-fixing plate 36. By forming the constricted portion 37 and/or the slit 48, the rigidity of the connection-fixing plate 36 decreases and it is possible to further increase the displacement amount at the front end of the connection-fixing plate 36. Furthermore, in the case of the piezoelectric/electrostrictive device 11D shown in FIG. 10(d), it is preferable to form the slit 48 at the front end side of the connection-fixing plate 36, preferably at the front end side of the joint between the diaphragm 32 and the connection-fixing plate 36 because the weight of the piezoelectric/electrostrictive device 11D itself can be decreased without greatly changing characteristics of the piezoelectric/electrostrictive device.

Figure 11A:
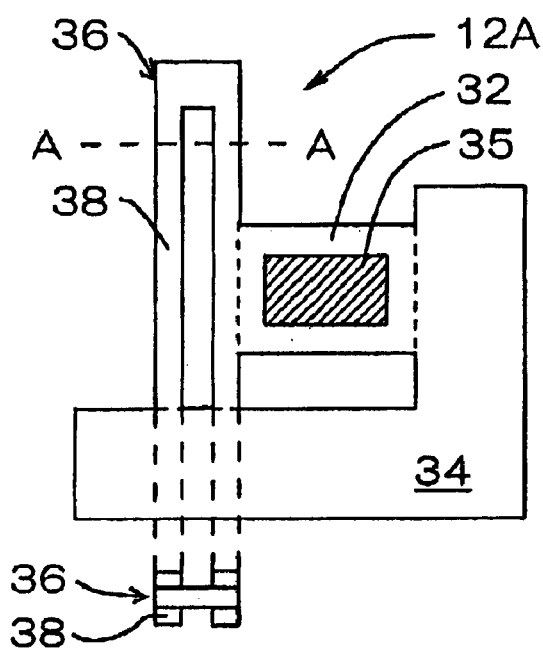
FIGS. 11(a)–(b) show top views of still another embodiment of a piezoelectric/electrostrictive device of the present invention.
Figure 11B:
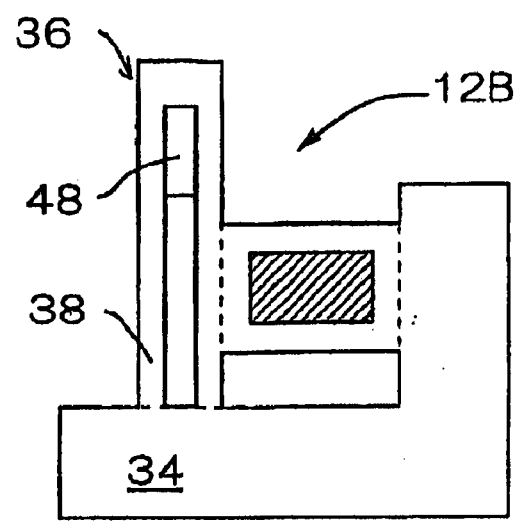

FIG. 11(a) shows a top view of a piezoelectric/electrostrictive device 12A in which the shape of the above connection-fixing plate 36 is changed and a sectional view taken along the broken line A—A of the top view. The connection-fixing plate 36 of the piezoelectric/electrostrictive device 12A is formed so that the circumferential portion of the connection-fixing plate is thicker than the central portion of connection-fixing plate. The shape of the connection-fixing plate 36 can be regarded as a structure constituted by thinning the central portion of the connection-fixing plate 36 of the piezoelectric/electrostrictive device 11A, and the fixing plate can be obtained by bonding a predetermined U-shaped spring plate 38 to the plane of a thin connection-fixing plate. The piezoelectric/electrostrictive device 12A is strong against twist though it is decreased in weight. Therefore, it is possible to improve the positioning speed (improvement of displacement-amount controllability) and the displacement (movement) path accuracy. Moreover, as the piezoelectric/electrostrictive device 12B shown in the top view of FIG. 11(b), it is possible to form the slit 48 at a portion of the connection fixing-plate 36 of the piezoelectric/electrostrictive device 12A where there is not the spring plate 38 (hollow portion inside of the U-shaped spring plate 38) and thereby, it is possible to increase a displacement amount.

Figure 25:
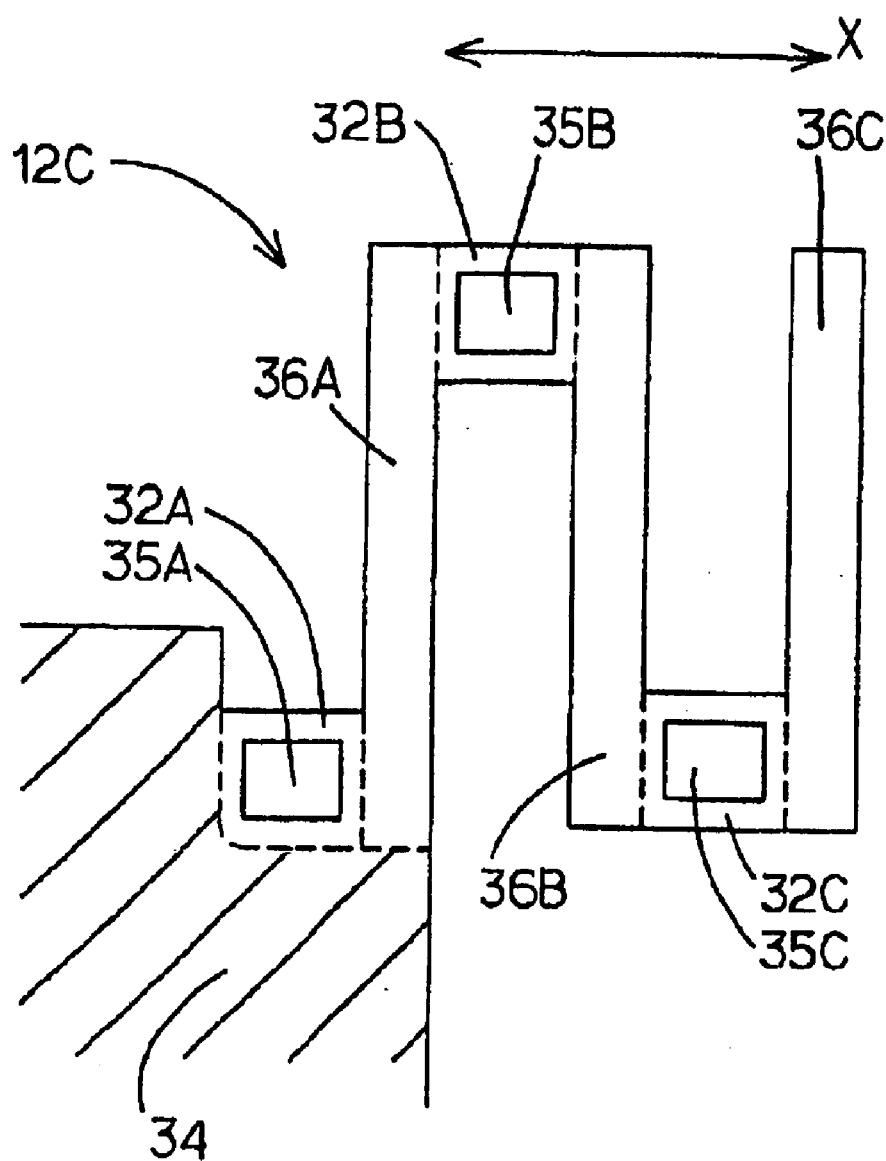
FIG. 25 shows a top view of still another embodiment of a piezoelectric/electrostrictive device of the present invention.

FIG. 25 is a top view of still another piezoelectric/electrostrictive device 12C using the above connection-fixing plate 36, showing an embodiment constituted by joining other diaphragm on which a piezoelectric element is formed to one end of a fixing plate at their sides and alternately joining necessary numbers of other connection plates and/or other fixing plates and still other diaphragms with the above other diaphragm at their sides.

That is, the piezoelectric/electrostrictive device 12C has a structure in which a first diaphragm 32A and a first connection-fixing plate 36A are joined to a side of the substrate 34, a second diaphragm 32B is joined to the side of the open side (normal fixing plate setting side) of the first connection-fixing plate 36A, and second connection-fixing plate 36B, third diaphragm 32C, and third connection-fixing plate 36C are successively joined to the second diaphragm 32B at their sides. Thus, by driving piezoelectric elements 35A to 35C arranged on the first to third diaphragm, it is possible to increase the displacement amount of the third connection plate 36C in the X-axis direction in FIG. 25.

The above structure can be also regarded as a structure obtained by successively joining a unit comprising a set of a diaphragm and a connection-fixing plate such as the second diaphragm 32B and the second connection-fixing plate 36B. Therefore, to obtain a predetermined displacement amount, it is only necessary to properly set the number of units to a preferable number.

Figure 12:
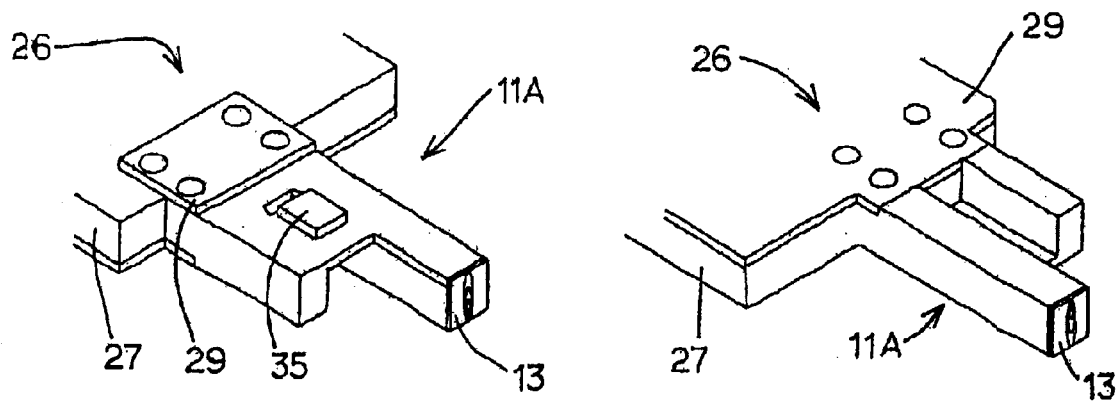
FIG. 12 shows perspective views of an embodiment of an actuator to which a piezoelectric/electrostrictive device of the present invention is applied.

FIG. 12 shows perspective views of an actuator 26 using the above-described piezoelectric/electrostrictive device 11A. The piezoelectric/electrostrictive device 11A is firmly fixed to a member such as a slider 27 by a fixing jig 29 or the like. A magnetic head 13 is set to the front end of the connection-fixing plate 36 of the piezoelectric/electrostrictive device 11A and it is possible to move the head 13 by a predetermined displacement amount by driving the piezoelectric element 35. Moreover, it is possible to unite a member to be fixed such as the slider 27 and the piezoelectric/electrostrictive device 11A into one body by processing green sheets to be described later without using the fixing jig 29.

Figure 13:
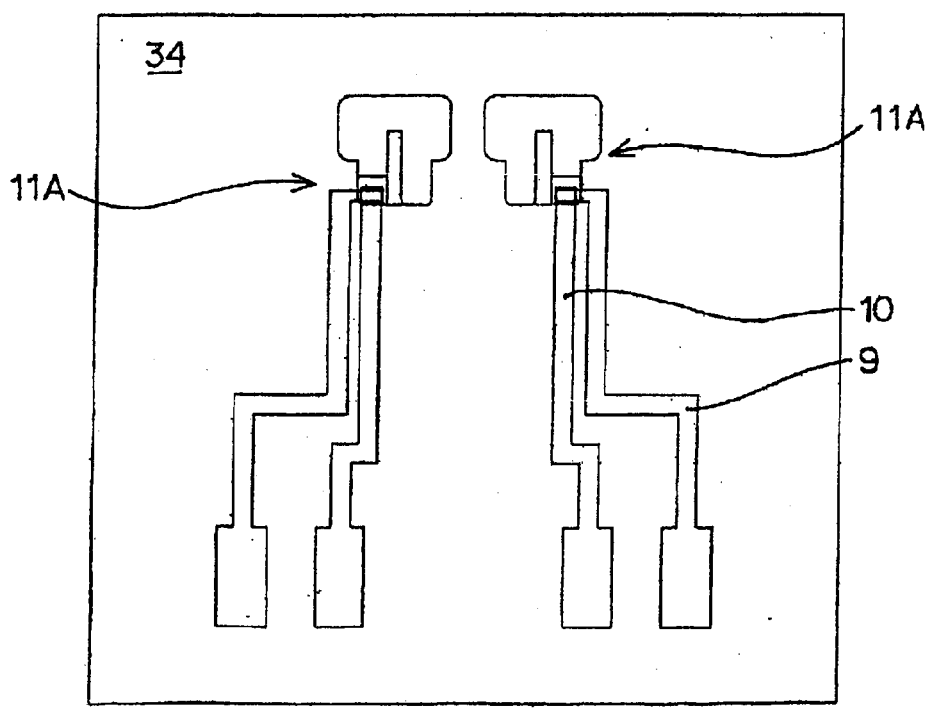
FIG. 13 shows a top view of still another embodiment of a piezoelectric/electrostrictive device of the present invention.

FIG. 13 shows an embodiment obtained by setting the piezoelectric/electrostrictive device 11A to two places in the substrate 34. It is possible to use the piezoelectric/electrostrictive devices 11A set to two places for the same purpose or different purposes at the same time and for a purpose of setting one piezoelectric/electrostrictive device 11A as a spare when the other piezoelectric/electrostrictive device 11A is broken. Therefore, it is possible to set a plurality of piezoelectric/electrostrictive devices of the present invention in one substrate and the setting positions of them are not restricted to the transverse parallel position shown in FIG. 13.

Figure 14:
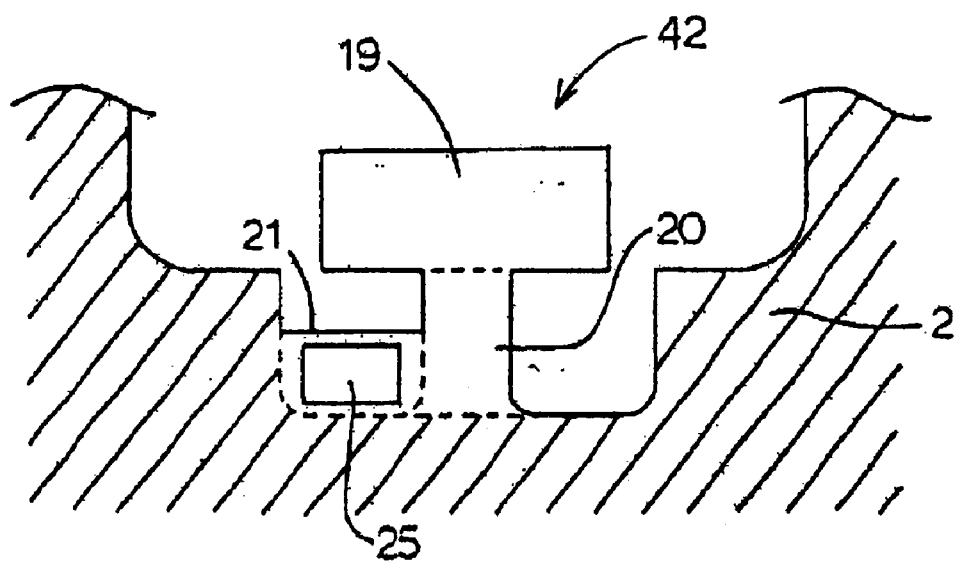
FIG. 14 shows a top view of still another embodiment of a piezoelectric/electrostrictive device of the present invention.

FIG. 14 is a top view of still another embodiment of a piezoelectric/electrostrictive device of the present invention. The above-described piezoelectric/electrostrictive device 30 has a structure in which the diaphragm 32 and the substrate 34 are joined each other only by one side. In the case of a piezoelectric/electrostrictive device 42, however, a diaphragm 21 and a substrate 2 are joined each other by two sides and one side is joined to a connection plate 20. By applying the above structure, it is possible to control the bending of the connection plate 20 and/or a spring plate 18 and easily cause a θ-mode displacement in the fixing plate 19.

Figure 15A:
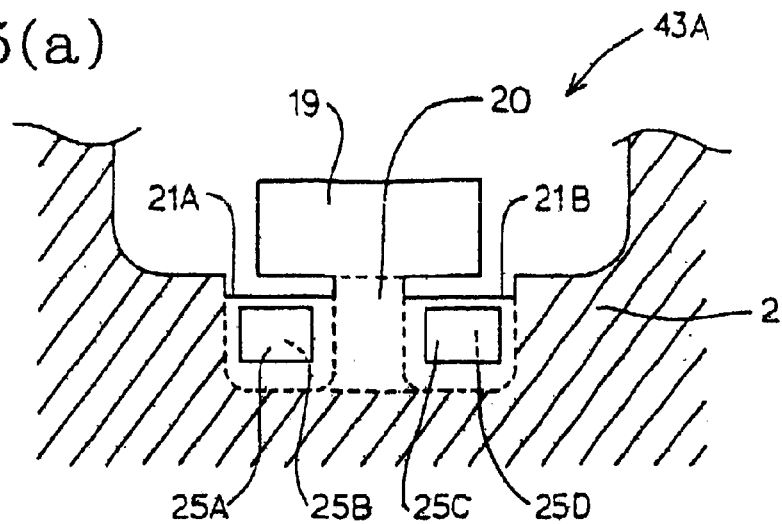
FIGS. 15(a)–(c) show top views of still another embodiment of a piezoelectric/electrostrictive device of the present invention.
Figure 15B:
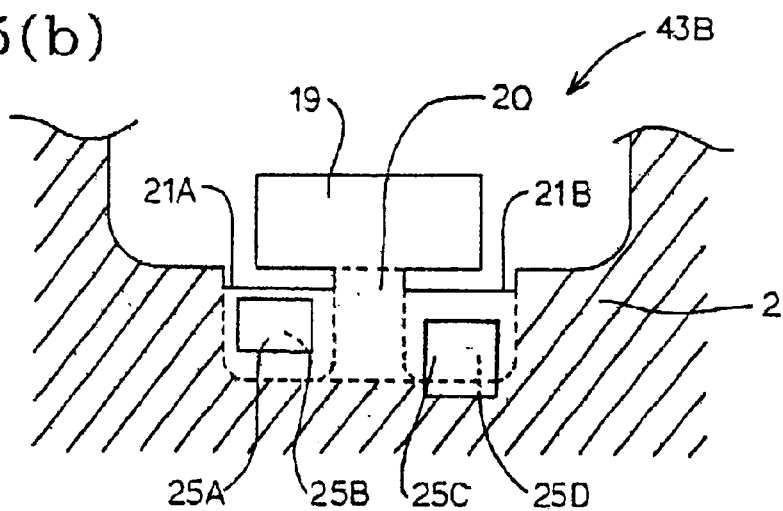
Figure 15C:
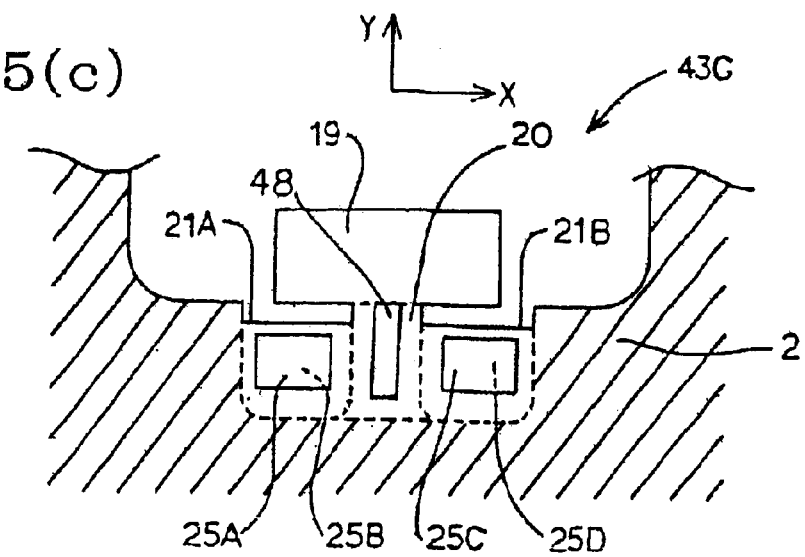

FIGS. 15(a) to 15(c) are top views of piezoelectric/electrostrictive devices 43A to 43C showing still another embodiment. First, the piezoelectric/electrostrictive device 43A shown in FIG. 15(a) has a structure in which a connection plate 20 and a fixing plate 19 are joined to each other at their sides, two diaphragm 21A and 21B are joined to the connection plate 20 at their sides so as to hold the connection plate 20 in the direction perpendicular to the direction of connection between the fixing plate 19 and the connection plate 20, and moreover, the diaphragm 21A and 21B are also joined to the substrate 2 similarly to the case of the diaphragm 21 shown in FIG. 14 and supported and fixed by three sides. By this structure, three-dimensional displacement modes such as the bending mode and the axis rotation mode of the fixing plate 19 are restricted. Moreover, it is not always necessary to join the diaphragm 21A and 21B to the substrate 2 at the bottom of the concave potion of the substrate 2.

In the case of the piezoelectric/electrostrictive device 43A, four piezoelectric elements 25A to 25d are formed on the both planes of the 21A and 21B. By properly assigning these piezoelectric elements to the driving element and auxiliary element for the fixing plate 19, more-accurate displacement control is realized.

Then, the piezoelectric/electrostrictive device 43B shown in FIG. 15(b) has a structure obtained by superimposing at least one of the piezoelectric elements 25A to 25D of the piezoelectric/electrostrictive device 43A, for example, at least one direction of the piezoelectric elements 25C and 25D on one side or two sides of substrate-2 side of the above three-side-supported diaphragm. In this case, it is preferable to use the piezoelectric elements 25C and 25D as auxiliary elements for measurement such as displacement-amount detection or troubleshooting because high-accuracy measurement is realized. Even when displacing setting positions of the piezoelectric elements 25A to 25D, it is necessary that the piezoelectric elements 25A to 25D do not overhang the connection plate 20 or a spring plate when the spring plate is used.

When bonding a spring plate to the connection plates 20 of the piezoelectric/electrostrictive devices 43A and 43B, it is possible to use a spring-plate reinforcement portion or reinforcement plate similarly to the case of the piezoelectric/electrostrictive device 40B. In this case, it is necessary to form the reinforcement plate so that it is joined at three sides of the substrate 2 serving as joining sides between the diaphragm 21A and 21B, connection plate 20, and substrate 2.

The piezoelectric/electrostrictive device 43C shown in FIG. 15(c) is an embodiment constituted by forming a slit 48 at the central portion in the longitudinal direction of the connection plate 20 of the piezoelectric/electrostrictive device 43A. The slit 48 is hollow and has a function for increasing the displacement amount of the diaphragm 19 and easily causing displacement or oscillation in ν mode or νz mode.

Here, the ν mode represents a mode in which the diaphragm 19 displaces so as to swing in the X-axis direction. When comparing the ν mode with the θ mode, the θ mode shows a pendulum-like displacement in the X-Y plane and has a Y-axis-directional component. In the case of the ν mode, however, a uniaxial-directional displacement in the X-axis direction in the X-Y plane is dominant and different from the θ mode in that it hardly has a Y-axis-directional component. Moreover, the νz mode represents a mode greatly displacing in the Z-axis direction (direction vertical to the X-axis and the Y-axis) as the diaphragm 19 away from the Y-axis in the displacement mode in the ν mode. When comparing the νz mode with the φ mode, it is different from the φ mode in that it hardly has a Y-axis directional component.

Because of the above displacement mode, it is difficult to use the ν mode and the νz mode for static displacement control. However, it is possible to use the modes for a dynamic displacement such as oscillation and a displacement caused by an external stress.

Figure 16A:
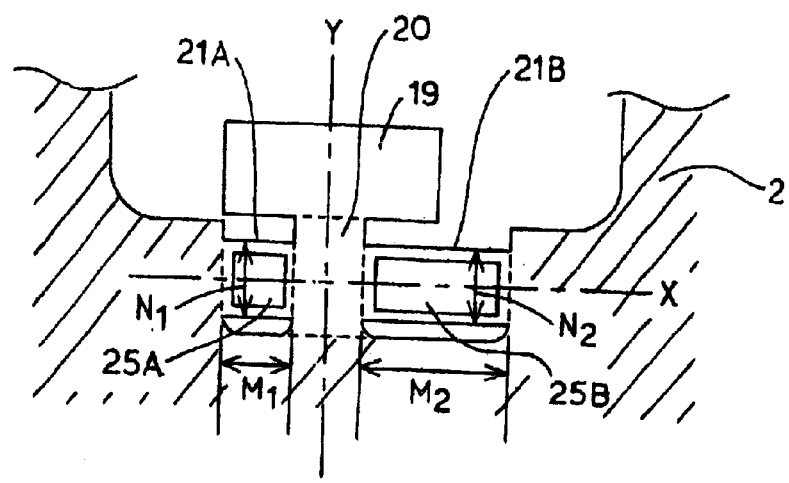
Figure 16B:
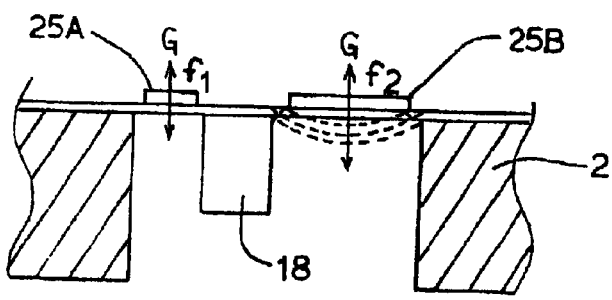

When setting a diaphragm to two places so as to hold a connection plate as shown in the case of the piezoelectric/electrostrictive devices 43A to 43C, it is possible to change the lengths $N_1$ and $N_2$ of the diaphragm 21A and 21B and the widths $M_1$ and $M_2$ of them and thereby increase the driving force of the fixing plate 19 by increasing the area of one diaphragm and preferably use the other diaphragm as an auxiliary element such as a displacement monitor by decreasing the area of the other diaphragm as shown by the top view in FIG. 16(a). Moreover, when changing the widths $M_1$ and $M_2$ of the diaphragm 21A and 21B, it is possible to improve the displacement accuracy and measurement accuracy by changing proper oscillation number of the bending displacement mode {arrow G in FIG. 16(b)) of the diaphragm 21A and 21B determined by the piezoelectric elements 25A and 25B and the diaphragm 21A and 21B to $f_1$ and $f_2$ and using one as a driving element and the other as an auxiliary element. It is preferable to use a piezoelectric element having smaller one of the proper oscillation number $f_1$ and $f_2$ as a driving element and a piezoelectric element having larger one of the frequencies $f_1$ and $f_2$ as an auxiliary element.

Figure 17:
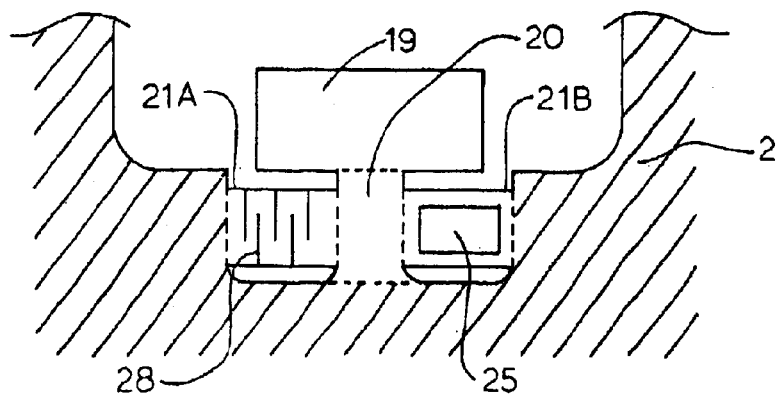
FIG. 17 shows a top view of still another embodiment of a piezoelectric/electrostrictive device of the present invention.

As shown by the case of the piezoelectric/electrostrictive devices 43A to 43C shown in FIG. 15 or 16, when setting a diaphragm to two places so as to hold a connection plate, it is more preferable to form a structure in which at least either of the piezoelectric elements 25C and 25D is formed on one diaphragm such as the diaphragm 21B and one slit 28 or preferably more slits 28 is or are formed on the other diaphragm 21A in the direction vertical to the direction of joining between the diaphragm 21A and the connection plate 20 as shown in FIG. 17. By using the above structure, it is possible to restrict rotations and vibrations and make a displacement in the θ mode dominant.

Figure 18A:
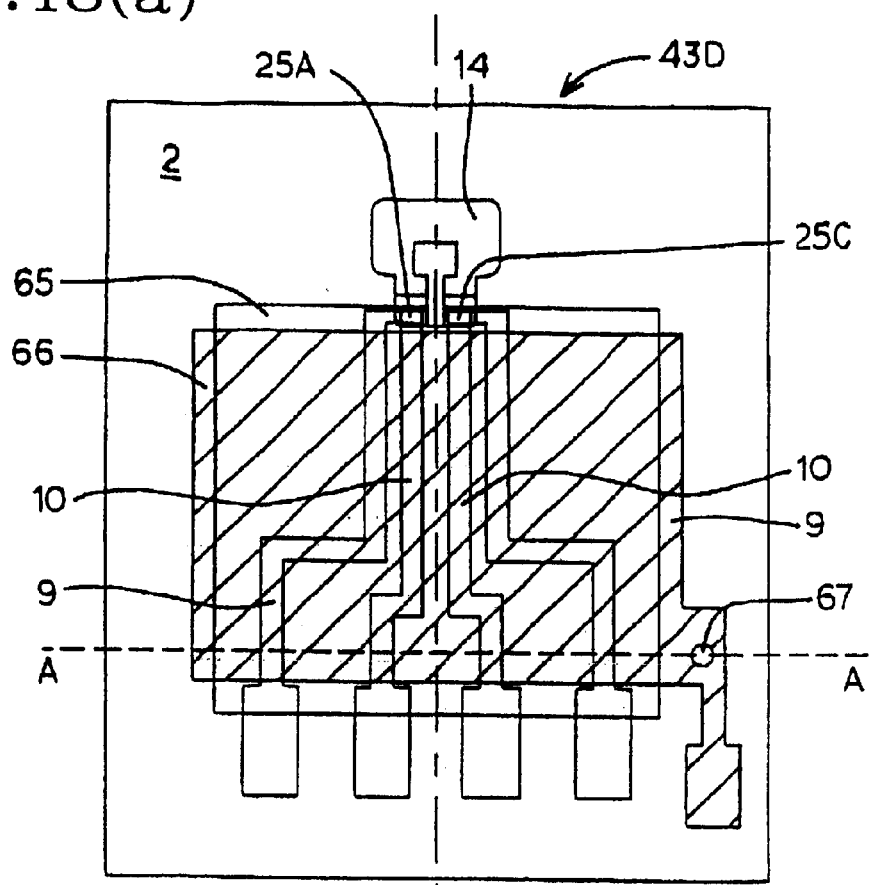
Figure 18B:
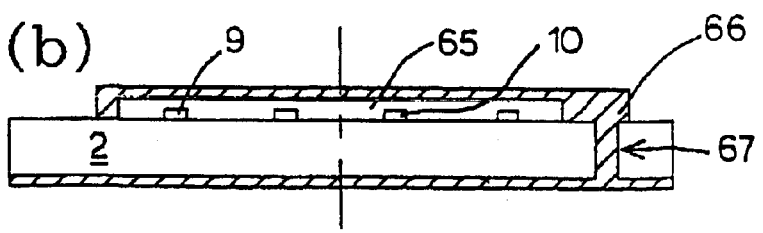
Figure 18C:
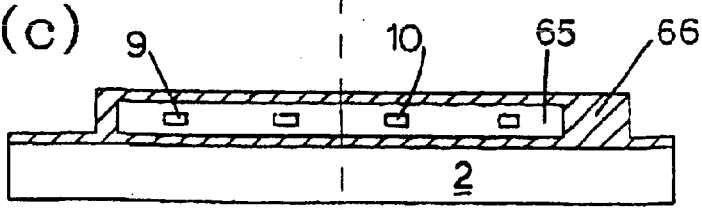
Figure 18D:
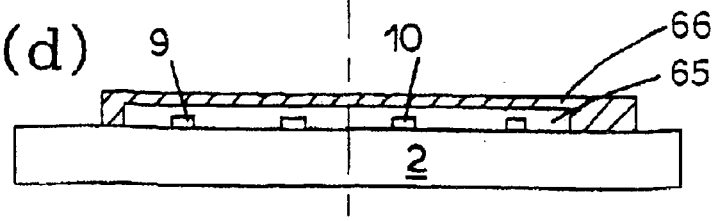

FIG. 18(a) shows a top view of a piezoelectric/electrostrictive device 43D in which the piezoelectric/electrostrictive device 43A of FIG. 15(a) is formed on the through-hole 14 of a substrate 2 and FIGS. 18(b) to 18(d) show sectional views taken along the broken line A—A in FIG. 18(a). In the case of the piezoelectric/electrostrictive device 43D, two piezoelectric elements 25A and 25C are arranged and provided with electrode leads 9 and 10. Moreover, an insulating coating layer 65 is formed so as to cover the piezoelectric elements 25A and 25C and the electrode leads 9 and 10. The insulating coating layer 65 respectively have a function for effectively preventing the piezoelectric elements 25A and 25C and the electrode leads 9 and 10 from being short-circuited when using a fixing plate 19 and the piezoelectric elements 25A and 25C in a liquid atmosphere or humidified atmosphere.

Furthermore, a shielding layer 66 made of a conductive material is formed on the piezoelectric/electrostrictive device 43D so as to cover the insulating coating layer 65 and formed on the both sides of the substrate 2 through a through-hole 67. The shielding layer 66 has functions for cutting off external electromagnetic waves when operating a piezoelectric/electrostrictive device at a high frequency or detecting high-frequency oscillation to preferably secure the displacement accuracy and moreover preventing erroneous operations from occurring or noises from mixing.

Configurations of setting the shielding layer 66 include the configuration of forming the shielding layer 66 so as to hold the substrate 2 as shown in FIG. 18(b), the configuration of enclosing only the wiring portion on the substrate 2 as shown in FIG. 18(c), and the configuration of shielding the wiring portion with only upper either side. Particularly, however, the configuration of shielding the entire wiring portion shown in FIGS. 18(b) and 18(c) is preferable. In FIG. 18(a), shielding layers 66 formed on the planes of the substrate 2 are electrically connected by using a through-hole 67. However, it is also possible to electrically connect them by using a side of the substrate 2. Details of materials preferably used to form the insulating coating layer 65 and the shielding layer 66 are described when the material of a piezoelectric/electrostrictive device is described later.

Figure 19A:
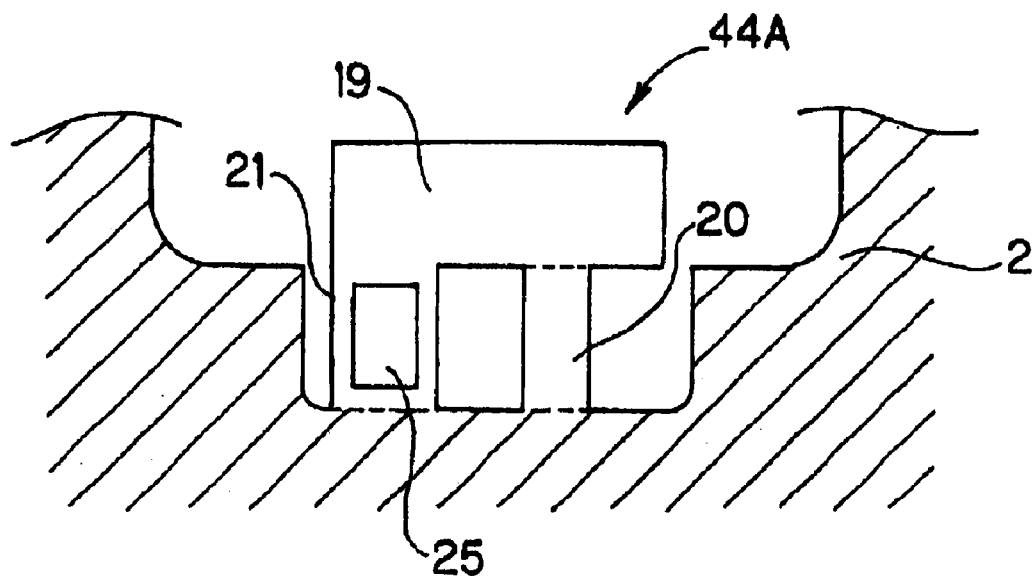
FIGS. 19(a)–(b) show top views of still another embodiment of a piezoelectric/electrostrictive device of the present invention.
Figure 19B:
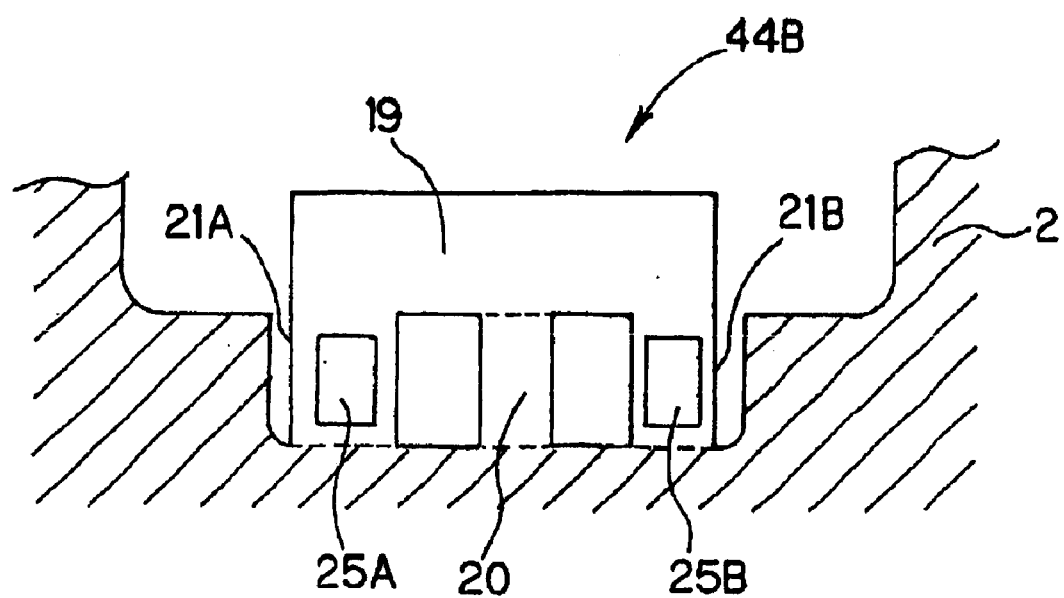

FIGS. 19(a) and 19(b) are top views of embodiments of still another piezoelectric/electrostrictive devices of the present invention. The piezoelectric/electrostrictive device 44A shown in FIG. 19(a) has a structure in which a connection plate 20 and a diaphragm 21 with a piezoelectric element 25 set on it are joined to a fixing plate 19 at their sides in parallel without being joined each other and the connection plate 20 and the diaphragm 21 are joined to a side of a substrate 2 while the fixing plate 19 is not joined to the substrate 2. The diaphragm 21 also functions as the connection plate 20. However, the piezoelectric/ electrostrictive device 44B shown in FIG. 19(b) has a structure in which two diaphragm 21A and 21B are arranged at the both sides of a connection plate 20 and piezoelectric elements 25A and 25B are arranged on the diaphragm 21A and 21B.

The piezoelectric/electrostrictive devices 44A and 44B are suitable for displacement and measurement in the θ mode because the displacement of the fixing plate 19 easily occurs in the plane of the fixing plate 19 and rotation and vibration of the fixing plate 19 are restricted. Moreover, because a strain generated by the piezoelectric element 25 directly works on the fixing plate 19 through the diaphragm 21 or because of its inverse action, there is an advantage that the positional accuracy and sensing sensitivity are improved.

Figure 20A:
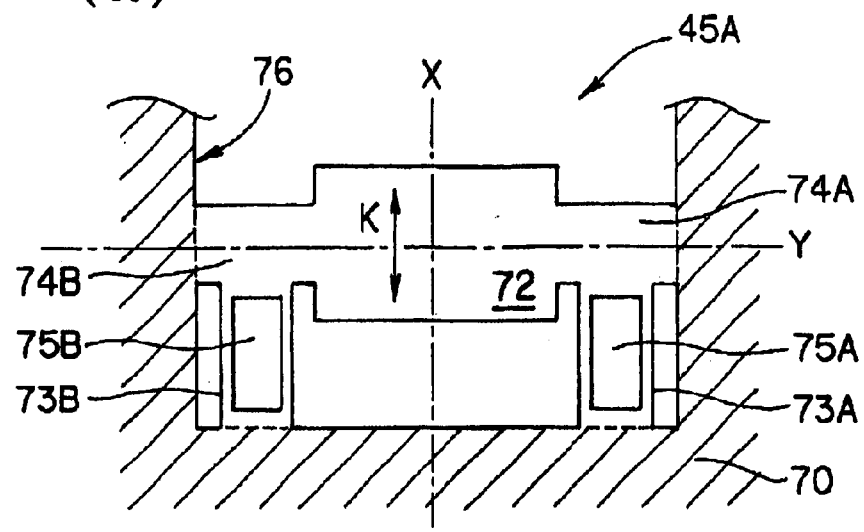
FIGS. 20(a)–(c) show top views of still another embodiment of a piezoelectric/electrostrictive device of the present invention.
Figure 20B:
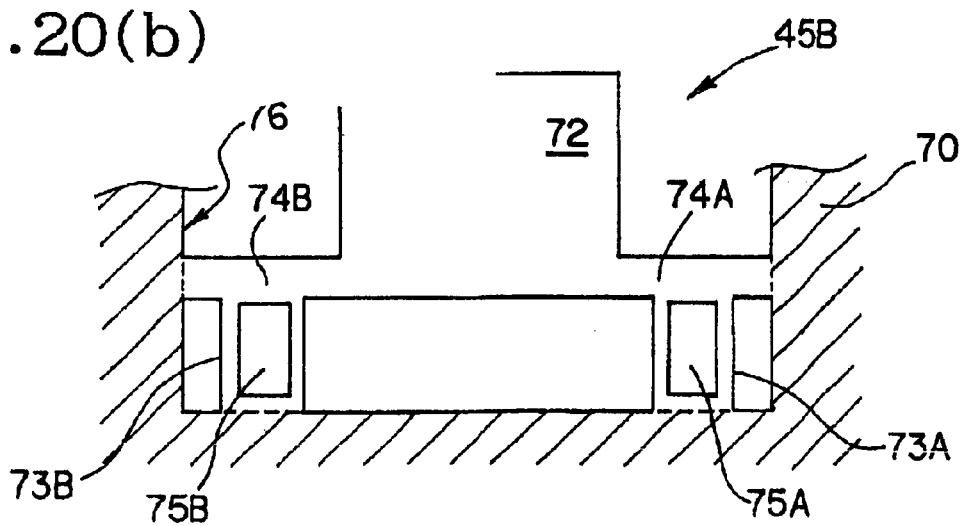
Figure 20C:
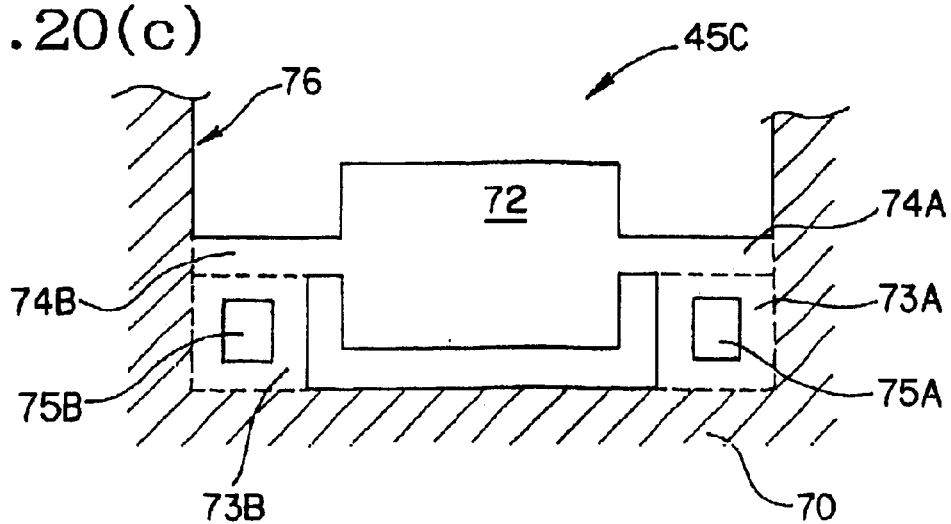

FIGS. 20(a) to 20(c) are top views of embodiments of still another piezoelectric/electrostrictive devices of the present invention. First, in the case of the piezoelectric/ electrostrictive device 45A shown in FIG. 20(a), a fixing plate 72 is joined to two connection plates 74A and 74B at their sides so as to be held by the connection plates 74A and 74B and sides of the connection plates 74A and 74B are set between the sides of a concave portion 76 of a substrate 70, two diaphragm 73A and 73B are set between the connection plates 74A and 74B and between the bottom sides of the concave portion 76 in the direction for the connection plates 74A and 74B to hold the fixing plate 72, that is, the direction perpendicular to the Y-axis direction, and moreover piezoelectric elements 75A and 75B are arranged on one plane of each of the diaphragm 73A and 74B. By using the above structure, an advantage is obtained that bending of the fixing plate 72 is controlled.

The concave portion 76 can use a side of the through-hole 14 formed on the substrate 2 previously shown in FIG. 18 or can be formed by cutting out a part of the outer periphery of the substrate 70. Moreover, the shape of the fixing plate 72 is not restricted to a rectangle. It is possible to use one of the fixing plates of optional shapes shown in FIGS. 6(a) to 6(d).

The piezoelectric/electrostrictive device 45B shown in FIG. 20(b) is constituted by joining a fixing plate 72 with connection plates 74A and 74B so as to separate the fixing plate 72 far from diaphragm 73A and 73B, which is effective to increase a displacement amount. Thus, a setting position of the fixing plate 72 can be optionally selected. Moreover, the piezoelectric/electrostrictive device 45C shown in FIG. 20(c) shows an embodiment in which diaphragm 73A and 73B are supported and fixed by connection plates 74A and 75B and a substrate 70 at three sides similarly to the case of the diaphragm 21 shown in FIG. 14.

These piezoelectric/electrostrictive devices 45A to 45C respectively have a preferable structure to perform displacement control or displacement-amount measurement in at least any one of the displacement modes such as the θ mode in which the fixing plate 72 displaces like a pendulum in the X-axis direction vertical to a side of the fixing plate 72 and vertical to the Y-axis centering around the Y-axis which is an axis vertically passing through the center of the fixed plane by using the joining face between the fixing plate 72 and the connection plate 74A or 74B, the φ mode in which the fixing plate 72 displaces like a pendulum centering around the Y-axis while a swing in the the X-axis direction is followed by a swing in the Z-axis direction (not illustrated) which is the direction parallel with a side of the fixing plate 72, a mode in which the fixing plate 72 displaces in the X-axis direction centering around the Y-axis shown by the bidirectional arrow K in FIG. 20(a) (hereafter, this mode is defined as "κ mode"), or a rotation mode in the plane of the fixing plate 72. Particularly, a stable displacement can be obtained in the κ mode.

Piezoelectric/electrostrictive devices 46A to 46F, which are still other embodiments of the present invention shown by top views in FIGS. 21(a) to 21(f) respectively, have a structure in which a fixing plate 72 is joined to two connection plates 74A and 74B at their sides so as to be held by the connection plates 74A and 74B, sides of the connection plates 74A and 74B are set between the sides of a through-hole 71 of a substrate 70 having through-holes, and at least a plurality of diaphragm, that is, diaphragm 73A to 73D in this case are set between the sides of the connection plates 74A and 74B and the through-hole 71 or the sides of the fixing plate 72 and the through-hole 71 in the direction vertical to the direction in which the fixing plate 72 is held by connection plates 74A and 74B. Piezoelectric elements 75A to 75D are optionally arranged on at least a portion on at least one plane of at least one of the diaphragm 73A to 73D.

In the case of each of the piezoelectric/electrostrictive devices 46A to 46F, when comparing the structure of the piezoelectric/electrostrictive device 46A with those of the piezoelectric/electrostrictive devices 45A to 45C shown in FIGS. 20(a) to 20(c), rotation of the fixing plate 72 centering around the Y-axis is restricted by the diaphragm 73A and 73B. Moreover, by forming the slit 28 on the diaphragm 73A and 73B similarly to the case of FIG. 17, the fixing plate 72 can easily displace in the direction of the arrow K, that is, a κ-mode displacement can be easily obtained.

The piezoelectric/electrostrictive device 46B is constituted by arranging the piezoelectric elements 75A to 75D on same-directional planes of all the diaphragm 73A to 73D. By using these piezoelectric elements as driving elements, it is possible to increase the displacement amount of the fixing plate 72 in the K direction. Moreover, the piezoelectric elements 75A to 75D can be provided for both planes of the diaphragms 73A to 73D and it is also preferable to use piezoelectric elements arranged in the same direction as auxiliary elements.

Figure 21A:
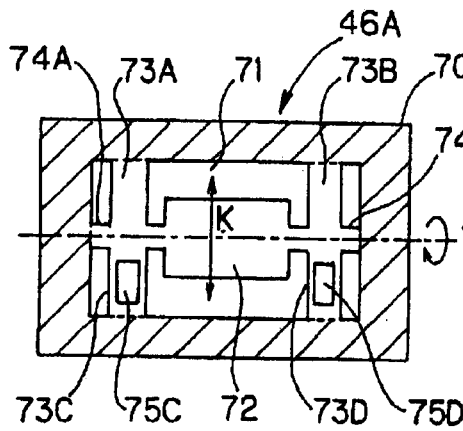
Figure 21B:
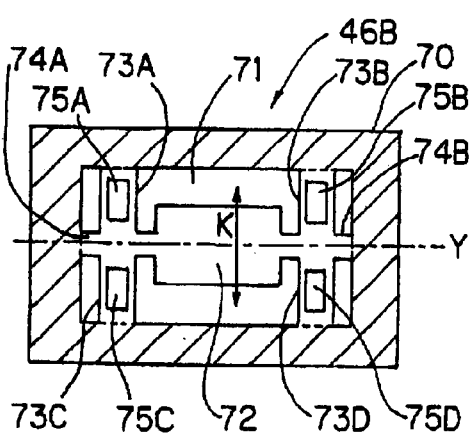
Figure 21C:
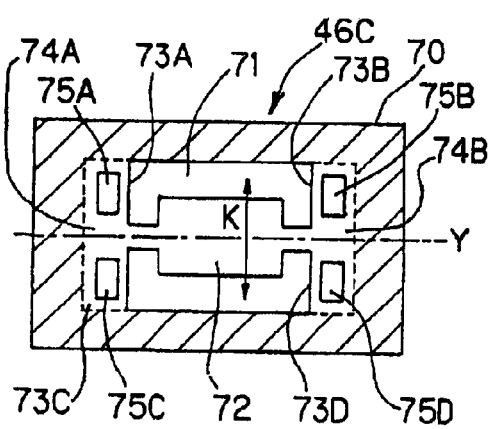
Figure 21D:
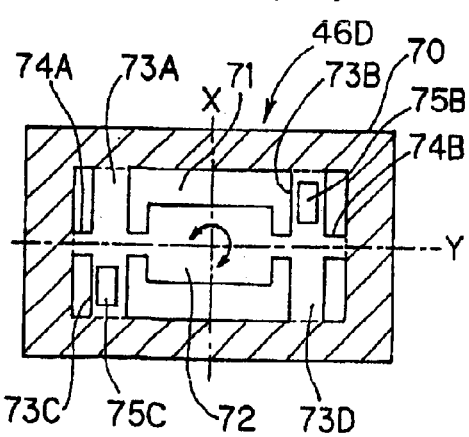
Figure 21E:
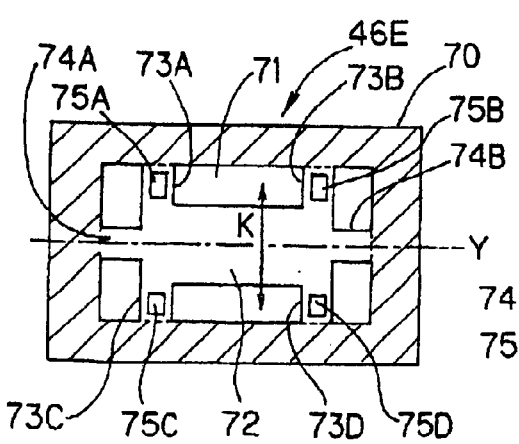
Figure 21F:
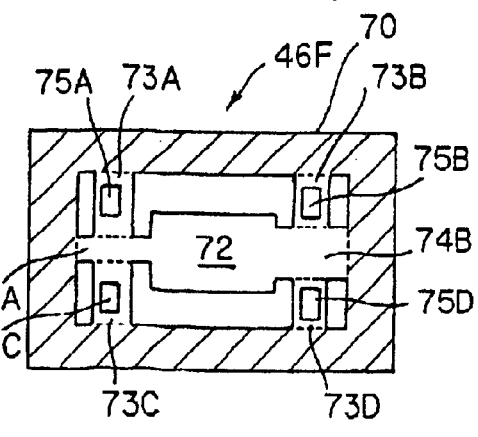

The piezoelectric/electrostrictive device 46C shows an embodiment formed so that sides of the diaphragm 73A to 73D in FIGS. 21(a) and 21(b) facing the substrate 70 are joined to the substrate 70. By using the above structure, it is possible to add the advantages obtained from the structure shown in FIG. 14 to those of FIGS. 21(a) and 21(b).

The piezoelectric/electrostrictive device 46D is constituted by arranging the piezoelectric elements 75B and 75C on the diaphragm 73B and 73C present at positions symmetric to the intersection between the X-axis and the Y-axis, which is the center of the fixing plate 72. In this case, as the displacement mode of the fixing plate 72, it is possible to use a displacement mode in which a displacement in the η direction {the direction of the bidirectional arrow in FIG. 21(d)} centering around the intersection between the X-axis and the Y-axis. Because the displacement mode is a rigid-body mode, it is not always necessary to form the diaphragm 73A and 73D. Moreover, when the diaphragm 73A and 73D are formed, it is possible to form the slit 28 or the piezoelectric elements 73A and 73D on the diaphragm 73A and 73D.

The piezoelectric/electrostrictive device 46E is constituted by joining the diaphragm 73A to 73D to the fixing plate 72, in which the setting state of the piezoelectric elements 75A to 75D is the same as the case of FIG. 21(*b*). By using the above structure, it is possible to generate or measure the displacement of the fixing plate 72 in the K mode. Moreover, the piezoelectric/electrostrictive device 46F has a structure to be easily displaced in the θ and φ modes by increasing one widths of the connection plates 74A and 74B and decreasing the other widths of them.

As described above, for piezoelectric/electrostrictive devices of the present invention, it is possible to select various shapes but materials used for piezoelectric/electrostrictive devices are not different in each piezoelectric/electrostrictive device. Then, materials constituting piezoelectric/electrostrictive devices of the present invention and shapes of the piezoelectric/electrostrictive devices are described. It is preferable that a substrate, fixing plate, connection plate (connection-fixing plate), diaphragm, spring plate, spring-plate reinforcement portion, and reinforcement plate are made of ceramics. For example, it is possible to use stabilized or partially-stabilized zirconia, alumina, magnesia, and silicon nitride. Among these substances, stabilized or partially-stabilized zirconia is most preferably used because it has a large mechanical strength, a high toughness, and a small reactivity with piezoelectric films and electrode materials.

However, when using the above stabilized or partially-stabilized zirconia as the material of the substrate and the like, it is preferable to constitute a diaphragm by adding at least an additive such as alumina or titania to the diaphragm.

It is not always necessary that such components constituting a substrate as a diaphragm plate, intermediate plate, base plate, fixing plate, connection plate (connection-fixing plate), spring plate, diaphragm, spring-plate reinforcement portion, and reinforcement plate are made of the same material. It is possible to use the above various types of ceramics for the above components by combining them in accordance with the design. However, it is preferable to integrally constitute the components by using the same material in order to secure the reliability of joints between portions and simplify the fabrication process.

To form a spring plate on the both planes of a connection plate, it is also possible to use a spring plate having the same structure as a piezoelectric element for a spring plate to be formed on the plane where piezoelectric elements are arranged. The above case is preferable from the viewpoint of the fabrication process because spring plates can be formed simultaneously with piezoelectric elements. However, the electrode of a piezoelectric element formed as a spring plate is not used as an electrode.

It is already described that the thickness and shape of a fixing plate of a piezoelectric/electrostrictive device of the present invention are not restricted and therefore, they are properly designed in accordance with the purpose. Moreover, the thickness of a substrate is properly determined by considering the operability. However, it is preferable to set the thickness of a diaphragm in a range of 3 to 20 μm and the total thickness of a diaphragm and a piezoelectric element in a range of 15 to 60 μm. Moreover, when using a spring plate, it is preferable to set the total thickness of a connection plate and a spring plate in a range of 20 to 300 μm and the width of them in a range of 30 to 500 μm, and the aspect ratio (width/thickness) of the spring plate in a range of 0.4 to 50 in any case of bonding the spring plate to either plane or both planes of a connection plate. Furthermore, when a spring-plate reinforcement portion is necessary, it is preferable to equalize the thickness of the portion with that of a spring plate to be bonded to the portion.

Then, though piezoelectric ceramics formed like a film is preferably used as a piezoelectric film of a piezoelectric element, it is also possible to use electrostrictive ceramics or ferroelectric ceramics. Moreover, it is possible to use a material requiring polarization or a material not requiring polarization. However, when using the piezoelectric/electrostrictive device in this invention for a recording head, it is preferable to use a material having a small strain hysteresis because the linearity between the displacement amount of a fixing plate and the driving or output voltage is important. Therefore, it is preferable to use a material having a coercive electric field of 10 kV/mm or lower.

Specifically, as the ceramics used for the piezoelectric film, the following are listed: lead zirconate, lead titanate, lead magnesium niobate, lead nickel niobate, lead zinc niobate, lead manganese niobate, lead antimony stannate, lead manganese tungstate, lead cobalt niobate, and barium titanate or ceramics containing a component obtained by combining some of the above materials. Among these materials, a material mainly containing a component consisting of lead zirconate, lead titanate, and lead magnesium niobate is preferably used for the present invention because the material has a high electromechanical coupling factor and a high piezoelectric constant, and a small reactivity with a substrate member when sintering a piezoelectric film and therefore, a material consisting of a predetermined composition can be stably formed.

Moreover, it is possible to use ceramics obtained by properly adding oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth or tin, or combination of some of these materials, or other compounds to the above piezoelectric ceramics. Furthermore, it is preferable to control the coercive electric field and piezoelectric characteristic of the material which mainly consists of lead zirconate, lead titanate, and lead magnesium niobate with additives such as lanthanum and strontium.

Furthermore, it is preferable that the electrode of a piezoelectric element is constituted of metal that is solid at room temperature and that is superior in conductivity. For example, a single metal of aluminum, titanium, chromium, iron, cobalt, nickel, copper, zinc, niobium, molybdenum, ruthenium, palladium, rhodium, silver, tin, tantalum, tungsten, iridium, platinum, gold, or lead, or an alloy obtained by combining some of the above metals is used for the electrode. Moreover, it is possible to use the cermet obtained by dispersing the same material as a piezoelectric film or diaphragm in the above metallic materials.

Actual electrode-material selection is determined depending on a method for forming a piezoelectric film. For example, to form a first electrode on a diaphragm and then form a piezoelectric film on the first electrode through firing, it is necessary to use a high-melting-point metal such as platinum which does not change even at a piezoelectric-film firing temperature for the first electrode. However, because the second electrode formed on the piezoelectric film after the piezoelectric film is formed can be formed at a low temperature, it is possible to use a low-melting-point metal such as aluminum.

Moreover, it is possible to form electrodes by integrally firing a piezoelectric element. In this case, however, it is necessary to use a high-melting-point metal withstanding the piezoelectric-film firing temperature for both first and second electrodes. Furthermore, as shown in FIG. 3, to form the first and second electrodes 59 and 60 on a piezoelectric film 58, it is possible to form the both electrodes 59 and 60 by using the same low-melting-point metal. Thus, it is possible to properly select preferable first and second electrodes depending on a piezoelectric-film forming temperature represented by a piezoelectric-film firing temperature and a piezoelectric-element structure.

Then, insulating glass or resin is used as the material of an insulating coating layer to be formed on a piezoelectric element and an electrode lead. Here, to improve the performance of a piezoelectric/electrostrictive device so as not to interrupt a displacement, it is preferable to use resin instead of glass as the insulating coating material. Therefore, one of the following fluorocarbon resins superior in chemical stability are used: tetrafluoroethylene-resin Teflon (Teflon PTF made by Du Point Inc.), tetrafluoroethylene-hexafluoropropylene copolymer-resin Teflon (Teflon FEP), tetrafluoroethylene-perfluoroalkylvinylether-copolymer-resin Teflon (Teflon PFA), and PTFE/PFA-composite Teflon. Moreover, silicone resin (particularly, thermosetting silicone resin) is preferably used though it is inferior to the above fluorocarbon resins in corrosion resistance and weather resistance. Furthermore, it is possible to use epoxy resin or acrylic resin in accordance with the purpose. Moreover, it is preferable to form an insulating coating layer by using materials different from each other for a piezoelectric element and its vicinity or an electrode lead and its vicinity. Furthermore, it is also preferable to add inorganic and organic additives (filler) to an insulating resin to adjust the rigidity of a diaphragm and the like.

When forming an insulating coating layer, various metals such as gold, silver, nickel, and aluminum are used as the material of a shielding layer formed on the insulating coating layer. Moreover, it is possible to use every metallic material used for the electrode or the like of the above piezoelectric elements. Furthermore, it is possible to use conductive paste obtained by mixing metallic powder with resin.

Then, a piezoelectric/electrostrictive device fabrication method of the present invention is described below. Slurry is manufactured by adding and mixing a binder, solvent, and dispersant to ceramic powder of zirconia or the like serving as the material of a substrate, fixing plate, connection plate, connection-fixing plate, diaphragm, and spring plate. Then, the slurry is degassed and manufacturing green sheets or green tapes for a diaphragm plate, intermediate plate, and base plate respectively having a predetermined thickness by the reverse roll coater method or doctor blade method. Unless a spring plate 18 is used, it is unnecessary to make an intermediate plate. In this case, however, to keep the mechanical strength of a substrate, it is necessary to increase the thickness of a base plate by that of an intermediate plate. That is, though a green sheet for intermediate-plate is not manufactured, it is preferable to increase the thickness of a green sheet for base-plate by a value equal to the thickness of the green sheet for intermediate-plate.

Then, a through-hole 14 and a spring plate 18 are formed on a green sheet for intermediate-plate 17 as shown in FIG. 22 by using a mold or laser beam, and a green sheet for base-plate 15 is punched into a predetermined shape so that the through-hole 14 is formed. Manufactured green sheet for diaphragm-plate 3, green sheet for intermediate-plate 17, and green sheet for base-plate 15 are united into one body by superimposing these sheets in order at least one by one and firing them to manufacture a substrate. In this case, to superimpose these green sheets 3, 15, and 17, a hole portion 8 is previously formed to determine superimposing positions.

It is also possible to form the through-hole 14 and the diaphragm 21 on the green sheet for diaphragm-plate 3 in the green state. However, because the green sheet for diaphragm-plate 3 generally has a very small thickness of 3 to 20 μm, it is preferable to obtain a predetermined shape after forming a substrate and arranging piezoelectric elements by laser-beam processing to be mentioned later in order to secure the surface flatness and dimensional accuracy of the sheet 3 after sintering a diaphragm and the like to be formed in the green sheet for diaphragm-plate 3.

To arrange piezoelectric elements at the portion of the green sheet for diaphragm-plate 3 on where the diaphragm 21 is finally formed, there is a method of manufacturing a substrate and a piezoelectric film at the same time by manufacturing the piezoelectric film in accordance with the press molding method using a mold or the tape forming method using slurry and thereby superimposing the green piezoelectric film at the position of the green sheet for diaphragm-plate 3 on where the diaphragm is formed under applying a heat and a pressure, and then co-firing the piezoelectric film and substrate. In this case, however, it is necessary to previously form an electrode on the substrate or piezoelectric film by using a film forming method to be described later.

Though the temperature for firing a piezoelectric film is properly determined depending on the material constituting the piezoelectric film, it is generally set to 800° to 1,400° C., preferably set to 1,000° to 1,400° C. In this case, it is preferable to sinter the piezoelectric film under the existence of the evaporation source of the material of the piezoelectric film in order to control the composition of the piezoelectric film. Moreover, to sinter the piezoelectric film and the substrate at the same time, it is naturally necessary to match the firing conditions of both to each other.

When using the film forming method, it is possible to arrange piezoelectric elements at the position of diaphragm forming on a sintered substrate through one of a thick-film forming method such as the screen printing method, dipping method, and coating method and one of various thin-film forming methods such as the ion beam method, sputtering method, vacuum deposition, ion plating method, chemical vapor deposition method (CVD), and plating. Among these methods, in the case of the present invention, a thick-film forming method according to one of the screen printing method, dipping method, and coating method is preferably used to form a piezoelectric film. These methods make it possible to form a piezoelectric film by using paste or slurry mainly containing piezoelectric ceramic particles having an average particle size of 0.01 to 5 μm, preferably 0.05 to 3 μm and thus, a preferable piezoelectric operation characteristic is obtained.

For example, after sintering a manufactured substrate under a predetermined condition, a first electrode is printed at a predetermined position on the surface of a diaphragm plate and fired, then a piezoelectric film is printed and fired, and moreover a second electrode is printed and fired to arrange piezoelectric elements. Then, an electrode lead for connecting each formed electrode to a measuring instrument is printed and fired. In this case, when using platinum (Pt) as the first electrode, lead zirconate titanate (PZT) as the piezoelectric films, gold (Au) as the second electrode, and silver (Ag) as the electrode lead, at a certain sintering stage, a material sintered before the sintering stage is not re-sintered because the firing temperature in the firing process is set so as to successively lower. Thus, it is possible to prevent a trouble such as separation or cohesion of an electrode material or the like from occurring.

By selecting a proper material, it is possible to sinter each member of a piezoelectric element and electrode leads integrally at one time through successively printing them, and it is also possible to form each electrode at a low temperature after forming a piezoelectric film. Moreover, it is possible to form each member of a piezoelectric element and electrode leads through a thin film method such as the sputtering method or vacuum deposition method. In this case, heat treatment is not always necessary.

Thus, by forming a piezoelectric element through a film forming method, it is possible to integrally bond and arrange a piezoelectric element and a diaphragm without using any adhesive, to secure reliability and reproductibity, and simply integration. Moreover, in this case, it is possible to form a piezoelectric film into a proper pattern. As the forming method, it is possible to use the screen printing method, photolithography method, laser-beam processing method, or machining method such as slicing or ultrasonic processing.

Then, a diaphragm and a fixing plate are formed at a predetermined position on a manufactured substrate. In this case, it is preferable to cut out and remove the green sheet for diaphragm-plate 3 through the machining using the fourth harmonic wave of a YAG laser. Thus, it is possible to form the through-hole 14 while leaving the portions integrally joined to a substrate such as a fixing plate and a diaphragm shown in FIGS. 18(a) to 18(d). In this case, it is possible to adjust a displacement amount by adjusting the shapes of the fixing plate and diaphragm.

Moreover, as shown in FIG. 23, it is possible to obtain a predetermined displacement characteristic by using the first electrode 22 as an upper electrode and the second electrode 24 as a lower electrode and thereby once setting the piezoelectric element 25 on which the piezoelectric film 23 is formed between the upper and lower electrodes, thereafter removing the upper electrode through the fourth harmonic wave of YAG laser or machining, and adjusting the effective electrode area of the piezoelectric element and moreover adjusting the electrical characteristics including impedance of a piezoelectric/electrostrictive device. When the structure of the piezoelectric element 25 is the comb structure shown in FIG. 3 or 4, it is necessary to remove a part of either electrode or parts of both electrodes.

For the above machining, it is possible to use one of various machining methods suitable for the size and shape of a resonant portion such as laser-beam processing using a YAG laser, second or third harmonic wave of the YAG laser, excimer laser, or $CO_2$ laser, electron beam processing, and dicing (machining) in addition to the above machining using the fourth harmonic wave of the YAG laser.

Moreover, it is possible to fabricate a piezoelectric/electrostrictive device of the present invention by using the pressure molding method using a forming die or slip casting method, or injection molding method in addition to the fabrication method using the above green sheets. Also in these cases, a piezoelectric/electrostrictive device of the present invention is machined through machining such as cutting or grinding before and after firing, punching through laser-beam processing or pressing, or ultrasonic processing and formed into a predetermined shape.

It is possible to form an insulating coating layer to be formed over a piezoelectric element and an electrode lead of the piezoelectric/electrostrictive device thus fabricated by using glass or resin through the screen printing method, coating method, or spraying method. In this case, when using glass as a material, it is necessary to raise the piezoelectric/electrostrictive device up to approximately the softening temperature of glass. Moreover, because glass has a large hardness, it may interrupt displacement or oscillation. However, because resin is soft and only requires treatment such as drying, it is preferable to use resin. It is already described that fluorocarbon resin or silicone resin is preferably used as the resin for forming an insulating coating layer. When using one of these resins, however, it is preferable to form a primer layer corresponding to the resin used and the type of ceramics and form an insulating coating layer on the primer layer in order to improve the adhesion of the resin with base ceramics.

Then, in the case of formation of a shielding layer formed on an insulating coating layer, it is difficult to perform firing when the insulating coating layer is made of resin. Therefore, when using various metallic materials, the shield layer is formed by a method requiring no heat such as the sputtering method. However, when using conductive paste made of metallic powder and resin, it is possible to properly use the screen printing method and coating method. When forming the insulating coating layer with glass, it is also possible to screen-printing and firing metallic paste at a temperature at which the glass does not flow or lower.

The configuration, materials, and fabrication method of a piezoelectric/electrostrictive device of the present invention are described above in detail. However, it is needless to say that the present invention is not restricted to the above embodiments. It should be understood that the present invention can be modified, corrected, or improved in accordance with the knowledge of a person skilled in the art as long as a modified, corrected, or improved embodiment does not deviate from the gist of the present invention.

INDUSTRIAL APPLICABILITY

A piezoelectric/electrostrictive device of the present invention is characterized in that the structure is simple and thus, the device is easily reduced in size and weight and hardly influenced by external harmful vibrations, and allows both static and dynamic displacements to be accurately controlled by using a piezoelectric element. Moreover, the device has an advantage that it can be inexpensively fabricated by a simple fabrication method. Furthermore, the device has an advantage that a proper material can be used each time in accordance with the purpose because component materials can be selected in a wide range. Therefore, when the device is set in various actuators and sensors, high-accuracy control and measurement are realized and moreover, a superior advantage is obtained that the device contributes to reduction in size and weight of the actuators and sensors.

We claim:

1. A piezoelectric/electrostrictive device comprising:
   a substrate;
   at least one connection plate extending along a first direction and having a first end attached to a first portion of said substrate and an opposed second end;
   at least one fixing plate attached to said second end of said connection plate;
   at least one diaphragm having a first end attached to a second portion of said substrate and an opposed second end attached to one of said fixing plate and said connection plate; and at least one piezoelectric element arranged on at least a portion of a surface of said diaphragm.

2. The piezoelectric/electrostrictive device according to claim 1, wherein a slit or constricted portion is formed on the connection plate.

3. The piezoelectric/electrostrictive device according to claim 1, wherein the fixing plate, the connection plate, and the diaphragm are integrally formed from one diaphragm sheet, and the substrate is formed by laminating integrally said diaphragm sheet and a base sheet.

4. The piezoelectric/electrostrictive device according to claim 1, wherein a spring plate is bonded to at least one plane of the connection plate and joined to the substrate or a spring-plate reinforcement portion formed on the substrate.

5. The piezoelectric/electrostrictive device according to claim 4, wherein the spring plate is either formed integrally from an intermediate sheet interposed between and integrated with a diaphragm sheet and a base sheet for the substrate, or formed integrally with a spring-plate reinforcement portion formed integrally with a diaphragm sheet, and formed integrally with the connection plate.

6. The piezoelectric/electrostrictive device according to claim 4, wherein a reinforcement plate is included which is bonded to the spring plate and joined to a side of the substrate.

7. The piezoelectric/electrostrictive device according to claim 6, wherein the reinforcement plate is formed integrally with the spring plate and the substrate.

8. The piezoelectric/electrostrictive device according to claim 2, wherein by using as a center axis a vertical axis passing vertically through the center of a fixed plane which is a connection surface between the fixing plate and the diaphragm, the piezoelectric/electrostrictive device operates in accordance with at least either of a θ-mode displacement in which the fixing plate displaces like a pendulum in a direction vertical to a side of the fixing plate and vertical to the vertical axis or a φ-mode displacement in which a swing in a direction vertical to a side of the diaphragm and vertical to the vertical axis centering around the vertical axis displaces like a pendulum while being followed by a swing in a direction parallel with the side of the fixing plate.

9. The piezoelectric/electrostrictive device according to claim 1, wherein at least a portion of the diaphragm is joined to the side of a through-hole formed in the substrate.

10. The piezoelectric/electrostrictive device according to claim 1, wherein the piezoelectric/electrostrictive element is divided into two piezoelectric elements, one used as a driving element, and the other used as an assistant element for driving the piezoelectric/electrostrictive device.

11. The piezoelectric/electrostrictive device according to claim 1, wherein at least two piezoelectric/electrostrictive elements are provided at different locations on the diaphragm, at least one of the piezoelectric/electrostrictive elements is used as a driving element and at least one of the remaining piezoelectric/electrostrictive elements is used as an assistant element for driving the piezoelectric/electrostrictive device.

12. The piezoelectric/electrostrictive device according to claim 1, wherein the piezoelectric/electrostrictive element and a lead used for joining electrically to an electrode of the piezoelectric/electrostrictive element are covered with an insulating coating layer made of a resin or a glass.

13. The piezoelectric/electrostrictive device according to claim 12, wherein the resin is a fluorocarbon resin or a silicone resin.

14. The piezoelectric/electrostrictive device according to claim 12, wherein a shielding layer made of a conductive material is further formed on the surface of the insulating coating layer.

15. The piezoelectric/electrostrictive device according to claim 1, wherein the substrate, the fixing plate, and the diaphragm are made of stabilized zirconia or partially-stabilized zirconia.

16. The piezoelectric/electrostrictive device according to claim 6, wherein the substrate, the fixing plate, the connection plate, the diaphragm, the spring plate, and the reinforcement plate are made of stabilized zirconia or partially-stabilized zirconia.

17. The piezoelectric/electrostrictive device according to claim 1, wherein a piezoelectric material forming the piezoelectric/electrostrictive element comprises at least one material selected from the group consisting of lead zirconate, lead titanate, and lead magnesium niobate.

18. The piezoelectric/electrostrictive device according to claim 1, wherein the shape of at least one of the fixing plate and the diaphragm is dimension-adjusted by trimming it through laser-beam machining or cutting.

19. The piezoelectric/electrostrictive device according to claim 1, wherein the electrode of the piezoelectric/electrostrictive element is laser-beam-machined or cut and thereby, the effective electrode area of the piezoelectric/electrostrictive element is adjusted.

20. The piezoelectric/electrostrictive device according to claim 1, further comprising a second diaphragm joined to at least one of said fixing plate and said connection plate, and a piezoelectric/electrostrictive element provided at least on a portion of at least one planar surface of said second diaphragm.

21. The piezoelectric/electrostrictive device according to claim 20, further comprising a second connection plate joined to said second diaphragm at one end of said second connection plate, and at least a third diaphragm joined to the other end of said second connection plate, and a piezoelectric/electrostrictive element provided at least on a portion of at least one planar surface of said third diaphragm.

22. The piezoelectric/electrostrictive device according to claim 21, further comprising a third connection plate joined to said third diaphragm at one end of said third connection plate.

23. The piezoelectric/electrostrictive device according to claim 1, wherein said diaphragm has a third side joined to said substrate.

* * * * *